US008444574B2

(12) United States Patent
List et al.

(10) Patent No.: US 8,444,574 B2
(45) Date of Patent: May 21, 2013

(54) LANCING SYSTEM FOR THE EXTRACTION OF A BODY FLUID

(75) Inventors: Hans List, Hesseneck-Kailbach (DE); Irio G. Calasso, Arth (CH); Joachim Hoenes, Zwingenberg (DE); Hans-Peter Haar, Wiesloch (DE); Uwe Kraemer, Ilvesheim (DE); Herbert Harttig, Neustadt (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 402 days.

(21) Appl. No.: 12/396,838

(22) Filed: Mar. 3, 2009

(65) Prior Publication Data
US 2010/0063417 A1 Mar. 11, 2010

Related U.S. Application Data

(63) Continuation of application No. PCT/EP2007/007434, filed on Aug. 24, 2007.

(30) Foreign Application Priority Data
Sep. 4, 2006 (EP) .................................. 06018498

(51) Int. Cl.
*A61B 5/00* (2006.01)
*A61B 17/32* (2006.01)
*A61B 17/14* (2006.01)
*B65D 81/00* (2006.01)

(52) U.S. Cl.
USPC ........... 600/583; 600/573; 600/576; 600/584; 606/167; 606/181; 606/182

(58) Field of Classification Search
USPC .................. 600/573, 576, 583, 584; 606/167, 606/170, 171, 172, 173, 181, 182, 183, 184, 606/185
See application file for complete search history.

(56) References Cited

U.S. PATENT DOCUMENTS
5,318,584 A 6/1994 Lange et al.
6,306,152 B1 10/2001 Verdonk et al.
(Continued)

FOREIGN PATENT DOCUMENTS
EP 0 199 484 A2 10/1986
EP 1 230 895 A1 8/2002
(Continued)

OTHER PUBLICATIONS
European Patent Application 05 027 428.1.
(Continued)

*Primary Examiner* — Sean P Dougherty
*Assistant Examiner* — Devin Henson
(74) *Attorney, Agent, or Firm* — Woodard, Emhardt, Moriarty, McNett & Henry LLP

(57) ABSTRACT

Lancing system comprising a needle and a lancing device The lancing device comprises a housing with a housing opening that is surrounded by a housing skin contact surface. A lancing depth reference element with a reference skin contact surface is adapted in such a manner that the reference skin contact surface at a reversal point of the lancing movement is in contact with the skin. The lancing depth is determined by the distance between the reference skin contact surface and the tip of the needle element at the reversal point of the lancing movement. The lancing depth reference element is in a stationary defined position relative to the reversal point of the lancing movement. The lancing depth reference element is adapted to stabilize the skin when pressed against the reference skin contact surface with respect to a skin deformation which occurs upon lancing of the skin.

39 Claims, 15 Drawing Sheets

U.S. PATENT DOCUMENTS

| | | |
|---|---|---|
| 6,929,650 B2 | 8/2005 | Fukuzawa et al. |
| 7,244,264 B2 * | 7/2007 | Roe et al. .................. 606/181 |
| 7,273,484 B2 | 9/2007 | Thoes et al. |
| 2004/0059256 A1 | 3/2004 | Perez |
| 2004/0127818 A1 | 7/2004 | Roe |
| 2004/0127819 A1 | 7/2004 | Roe et al. |
| 2004/0236251 A1 * | 11/2004 | Roe et al. .................. 600/583 |
| 2006/0100543 A1 | 5/2006 | Raney et al. |
| 2006/0155317 A1 * | 7/2006 | List .............................. 606/181 |
| 2006/0173380 A1 | 8/2006 | Hoenes et al. |
| 2008/0082023 A1 | 4/2008 | Deck et al. |
| 2008/0108910 A1 | 5/2008 | Hein et al. |
| 2008/0262388 A1 | 10/2008 | List et al. |

FOREIGN PATENT DOCUMENTS

| | | |
|---|---|---|
| EP | 1 504 718 A2 | 2/2005 |
| EP | 1 527 736 A1 | 5/2005 |
| EP | 1 669 028 A1 | 6/2006 |
| EP | 1 797 822 A1 | 6/2007 |
| WO | WO 02/100461 A2 | 12/2002 |
| WO | WO 2005/006985 A2 | 1/2005 |
| WO | WO 2006/092309 A2 | 9/2006 |

OTHER PUBLICATIONS

International Application No. PCT/EP2007/007434 International Search Report mailed Dec. 14, 2007.

European Patent Application No. EP 06 01 8498.3 Search Report mailed Feb. 14, 2007.

International Application No. PCT/EP2007/007434 International Preliminary Report on Patentability mailed Mar. 19, 2009.

International Application No. PCT/EP2007/007434 International Preliminary Report on Patentability Translation mailed Mar. 26, 2009.

* cited by examiner

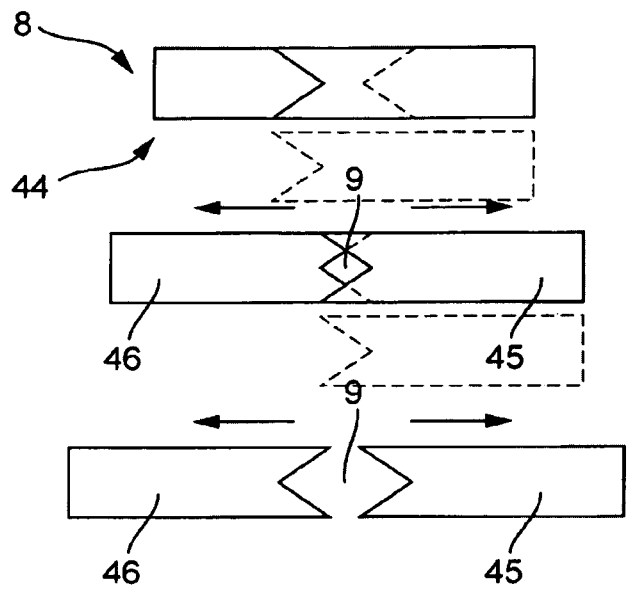
Fig. 9a
Fig. 9b
Fig. 9c
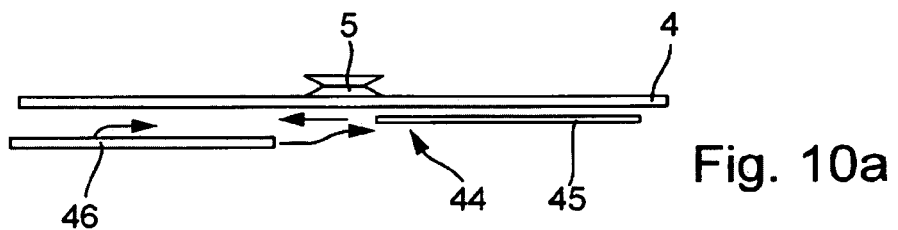
Fig. 10a
Fig. 10b

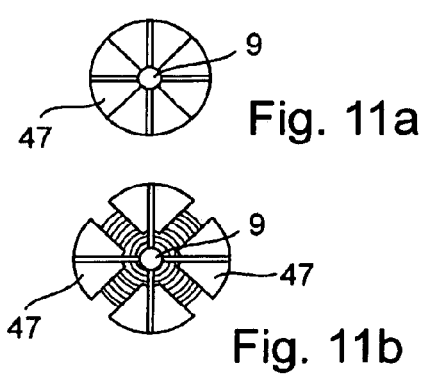
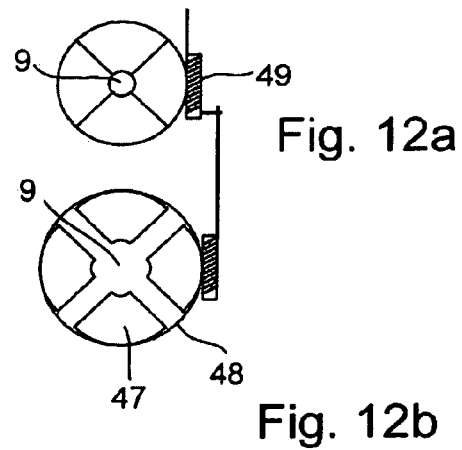
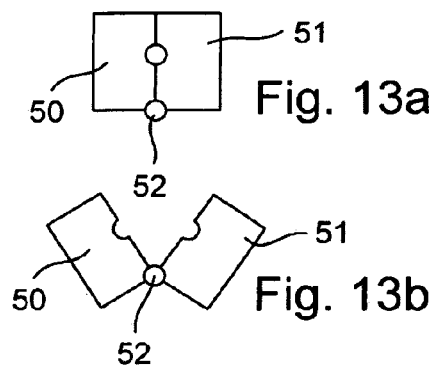
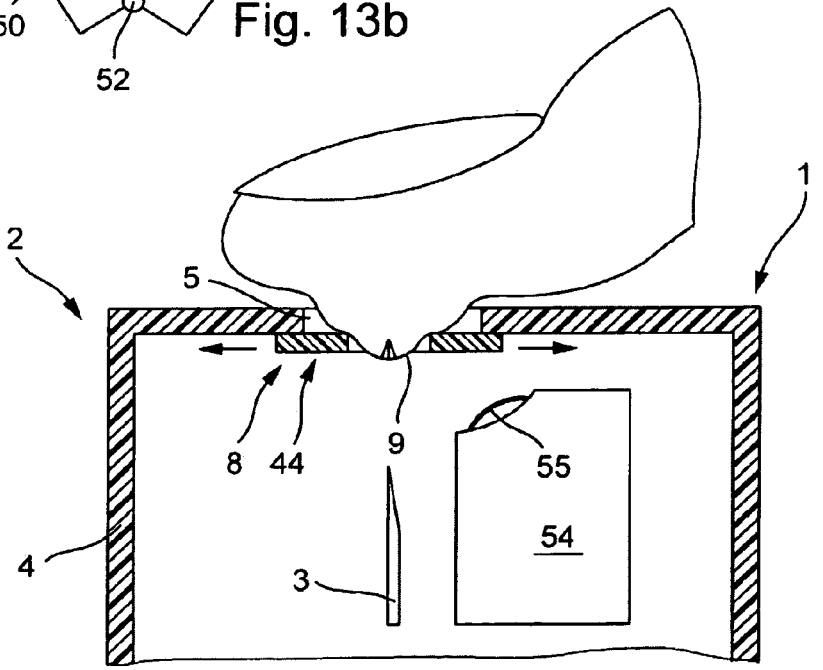
Fig. 14

US 8,444,574 B2

LANCING SYSTEM FOR THE EXTRACTION OF A BODY FLUID

CROSS REFERENCE TO PRIOR APPLICATION

This application is a continuation of International Application No. PCT/EP2007/007434, filed Aug. 24, 2007, which claims the benefit of European Application No. 06 018 498.3, filed Sep. 4, 2006, both of which are hereby incorporated by reference in their entirety.

BACKGROUND

The invention relates to a lancing system for the extraction of a body fluid from the skin of a human or animal. The lancing system comprises a needle element for lancing the skin and a lancing device, which includes a lancet drive. By the lancet drive a lancing movement is driven in a lancing direction of a needle element, the needle element being coupled with the lancet drive by means of a coupling mechanism.

Generally the body fluid extracted by means of the lancing system is blood. In some applications however, samples of interstitial fluid are also extracted. If blood as an example of a body fluid is mentioned hereafter, this is not a restriction of the generality. Blood stands only as an example for any other body fluid extractable from the skin.

For diagnostic purposes small quantities of blood are extracted from a body part, for example from the finger or the ear lobe. Lancets, which lance a wound in the body part with their tip, are used for this purpose. The prick of the lancet in the skin is performed either by specially trained personnel, who manually carries out the pricking, or by blood extraction systems, which include so-called lancing devices and lancets adapted therefor.

In the case of simple lancing devices the lancet pricks the skin with a quick movement and on reaching the reversal point is again withdrawn from the skin. After this the lancing device is removed. The user then massages the skin in the region of the prick and compresses it to promote the discharge of blood from the skin. This compression of the skin designated as "milking" is continued until an adequately large drop of blood issues from the skin. In a further step the drop of blood is applied to a test strip in order to determine the concentration of an analyte, in particular the glucose value, present in the blood. However, this procedure is tedious and also unpleasant for the user since he has to squeeze the skin in the vicinity of the wound.

In particular for diabetics who have to lance their skin repeatedly every day to determine the glucose content in the blood, lancing as free of pain as possible is important. Also important is a simplified handling of the blood extraction. Especially the "milking" which is perceived as unpleasant should be avoided. For this reason a plurality of lancing devices were developed in the prior art which comprise a large outlet opening for the lancet with a diameter of several millimeters. The front end of the housing enclosing the outlet opening in the shape of a ring forms a housing skin contact surface which is pressed against the skin. As a result of the pressure the skin bulges into the opening of the lancing device. At the same time, the internal pressure in the finger (or other body part) is increased by the contact pressure exerted, so that upon lancing of the skin by the lancet the body fluid or the blood issues spontaneously without manual massaging or "milking" being required. Products of this type are hereinafter referred to as "lancing system with expression aid".

It has been known for some time that the pain perception is substantially influenced by the reproducibility of the lancing depth. In other words, the depth of the prick is to remain preferably the same with a plurality of lancing operations (but unchanged setting of the lancing device) separated in time in order to generate an adequate quantity of blood with a minimum prick depth (U.S. Pat. No. 5,318,584). The prick depth is determined on the one hand by the position of the reversal point of the lancing movement and on the other hand by the position of the skin upon reaching of the reversal point. The reproducibility of the position of the reversal point depends on the construction of the lancet drive. Numerous drive constructions are known which guarantee a very good reproducibility of the position of the reversal point. These include in particular rotor drives as are described in U.S. Pat. No. 5,318,584 and numerous further documents of the prior art. The present invention can be combined with various drive constructions, provided these guarantee adequate reproducibility of the position of the reversal point with a plurality of lancing operations and unchanged setting of the device. With a given quality of the lancet drive the reproducibility of the prick depth decisively depends on a reproducibly defined position of the skin during the prick.

In this regard there are particular problems with lancing system with expression aid since the bulging-in of the skin is dependent on the condition of the skin and therefore varies from user to user. Even for a particular user, the skin changes its characteristics, for example as a function of whether it is dry or moist and cold or warm respectively. For this reason the housing skin contact surface on the inner edge of the housing opening constitutes only an inaccurate reference for the lancing depth.

To solve this problem a reference element is proposed in EP 1669028 A1 which, by means of a reference element coupling mechanism, is coupled with the drive of the lancing device and thus moveable. It is moved forward within the lancing device until a contact surface formed at its front end is in contact with the skin. Thereby the variation of the bulging-in of the skin into the housing opening is detected and the restriction of the reproducibility resulting from this variation, is eliminated. According to EP 1669028 the contact pressure between the reference element and the skin surface should be low since elevated pressure counteracts the issue of blood from the lancing wound. In addition it is emphasized that after the lancing the reference element should be moved away from the lancing wound very rapidly (within a maximum of 50 msec) in particular in order to avoid contamination of the reference element by issuing blood.

According to a series of further known proposals, function improvements, including the reproducibility of the lancing depth, are to be achieved by using a lancing depth control element rapidly moved towards the skin jointly with a needle, wherein positive effects are to be achieved by the impulse on impacting the skin.

For example EP 1527736 A1 discloses a lancing device wherein a lancing unit consisting of a lancet and a lancing depth control element is moved towards the skin. During the forward phase of the lancet movement, the lancing depth control element is moved therewith until it strikes the skin. Thereafter, the tip of the lancet penetrates into the skin.

A basically similar lancing device is disclosed in U.S. Pat. No. 6,306,152 B1. It comprises a relatively large housing opening through which the skin can bulge into the lancing device. In order to stretch the skin during the lancing it is proposed to employ a spring-loaded control element which jointly with the lancet is moved in the direction of the skin during the forward phase of the lancing movement. When the control element strikes the skin the lancet moveably mounted in the control element continues to be moved in the lancing direction by its inertia until it strikes a stop of the control element. Thereby it pricks the skin. The spring used to advance the control element then retracts the control element with the lancet, thereby extracting the lancet from the skin. U.S. Pat. No. 6,929,650 B2 also describes a system wherein the lancet on the way into the skin takes along a stop structure which contacts the skin and defines the lancing depth.

SUMMARY

Based on this it is the object of the invention to propose a lancing system with which the blood after the lancing issues from the skin without additional handling steps and the lancing takes place with the least pain possible for the patient. A system of this type should overcome the disadvantages known in the prior art.

The object is solved by a lancing system for the extraction of a body fluid from the skin of a body part of a human or animal with the features according to Claim 1.

The lancing system comprises a needle element for lancing the skin and a lancing device which includes a lancet drive. By the lancet drive a lancing movement of the needle element, which is coupled with the lancet drive by means of a coupling mechanism, is driven in the lancing direction. The lancing device has a housing with a housing opening at its, in lancing direction, front end. The housing opening is surrounded by a housing-contact surface which is pressed against the skin of the body part when the lancing device is used.

In an forward phase of the lancing movement the needle element is moved in a lancing direction along a predetermined lancing path until its tip enters the skin to create a wound. In a return phase of the lancing movement, after reaching a reversal point corresponding to the lancing depth in the skin, the needle element is retracted again. A predetermined value of the lancing depth is guaranteed by a lancing depth reference element with a reference skin contact surface, wherein the lancing depth reference element is adapted and arranged so that the reference skin contact surface is in contact with the skin at the reversal point of the lancing movement. The predetermined value of the lancing depth is determined by the distance in lancing direction between the reference skin contact surface and the position of the tip of the needle element at the reversal point of the lancing movement.

The lancing depth reference element with the reference skin contact surface is located in a defined stationary position with respect to the reversal point of the lancing movement at the time at which the tip of the needle element in the forward phase of the lancing movement passes the reference skin contact surface and enters a skin surface which is in contact with said reference skin contact surface. In addition, the lancing depth reference element is adapted and arranged in such a manner that deformation stabilization of the skin surface pressed against it is achieved. Due to this deformation stabilization the reproducibility of the lancing depth is not impaired to a practically interfering extent by the fact that the skin is locally deformed ("dented") when it is entered by the tip of the lancet.

The invention primarily deals with the problem of defining as accurately reproducible as possible the position of the skin surface actually relevant to the lancing depth and simultaneously guarantees a reliably adequate blood issue without additional "milking" of the finger. It is particularly characterized in that the following two features are combined with each other:

a) The lancing depth reference element—in contrast with the known lancing systems discussed above—is not moved jointly with the needle but it is located in a fixed (stationary) position relative to the reversal point of the lancing device. This applies at least at the time of lancing, i.e. when the tip of the needle element passes the reference skin contact surface in the forward phase of the lancing movement. Preferentially the reference element remains in the stationary position at least up to the time at which the needle element reaches the reversal point of its lancing movement. Particularly preferably the lancing depth reference element remains in its defined stationary position throughout the forward phase of the lancing movement of the needle element, i.e. from the triggering of the lancing movement to the reaching of the reversal point.

If the lancet drive is rigidly fixed in the housing of the lancing device the position of the reversal point of the lancing movement relative to the housing is fixed and consequently the reference element, also relative to the housing, stationary. However, according to a preferred embodiment of the invention, which will be explained in more detail later the lancing depth reference element and at least a part of the lancet drive are jointly mounted resiliently in such a manner that upon pressure on the reference skin contact surface they can perform a synchronous movement with constant distance in lancing direction. In this case the lancing depth reference element with the skin contact surface is not stationary relative to the housing, but is stationary relative to the reversal point of the lancing movement. However, in this case, too the lancing depth reference element is located in a practically stationary position relative to the housing throughout the forward phase of the lancing movement of the needle element since movements of the reference element (and the parts of the lancet drive jointly mounted resiliently with said reference element) caused by variation of the pressure on the reference skin contact surface are far slower than the lancing movement in its forward phase.

b) The lancing depth reference element is adapted and arranged in such a manner that when pressing the skin against the reference skin contact surface deformation stabilization is achieved. This term designates a tautening of the skin by which it is prevented that the reproducibility of the lancing depth is impaired in an interfering manner by a skin deformation which occurs when the tip of the needle element lances the skin. This is in particular guaranteed in that during the lancing an adequately large "deformation-stabilizing" compression force acts between the reference skin contact surface and the skin.

In a plurality of the above discussed prior art documents it is considered advantageous if the lancing depth reference element is moved in the direction of the skin together with the needle element and impacts the skin with a substantial impulse. In the context of the present invention it was discovered that with these known constructions the impact of the reference element on the skin causes a part-elastic impact effect by which the lancing pain is increased. This increased pain is, according to the present findings, not caused directly by the impacting of the reference element but is an indirect effect which is connected with variations of the lancet movement caused by the part-elastic impact. With the present invention this problem is avoided by the stationary positioning of the lancing depth reference element.

A substantial improvement compared with EP 1669028 discussed above is achieved by maintaining at the time of the lancing conditions which on the one hand effect the explained deformation stability and on the other hand impair the blood expression. In contrast with the known construction, the force with which the skin presses against the reference skin contact surface ("compressive force") at the time of lancing is in particular set to a sufficiently high deformation-stabilizing value. This can in particular be achieved in two manners:

a) By means of a force sensor which measures the compressive force. The measured compressive force can then be indicated to the user on a display so that said user triggers the lancing when the compressive force is between a minimum and a maximum value. Obviously triggering can also occur automatically. The pressure sensor is advantageously coupled with the lancing depth reference element. For example the lancing depth reference element can comprise a pressure sensor by means of which the contact pressure is determined. The sensor can be embodied mechanically, electrically or optically. Additional sensoric devices which determine the contact pressure of the skin against the reference skin contact surface are also conceivable. These need not necessarily be coupled with the lancing depth reference element.

b) To guarantee the desired skin-stabilizing compressive force the lancing depth reference element can be moveably mounted, wherein it is pressed by means of a spring device in lancing direction against a housing-fixed stop in such a manner that when the skin is pressed against its reference skin contact surface it is lifted off the stop and displaced backwards against the lancing direction and against the force of the spring device. Thereby the compressive force acting on the skin corresponds to the spring force of the spring device. The force of the spring device should be as stable as possible. This can be achieved for example by a preloaded metal spring having, in the movement range of the lancing depth reference element, a flat spring characteristic, but for example also by means of a gas spring.

Since the deformation-stabilizing effect depends on a plurality of factors including the dimensions of the components of the lancing device involved, it is not possible to make generally valid statements concerning the compressive force required. In practice it has been shown however that the desired effect occurs at a compressive force of at least 2 N, preferentially at least 3 N. On the other hand however the compressive force should not be too strong. Preferably its maximum value is 7 N, while values of at most 5 N are particularly preferred.

When using the lancing system according to the invention the user presses the skin of his body part, preferentially his finger against the device. In the process, the skin is pressed against the reference skin contact surface. By the contact pressure acting at the reference skin contact surface the skin is tautened before the tip of the needle element lances the skin. Denting of the skin is prevented. The pain perception of the user upon lancing is reduced and the reproducibility of the lancing depth improved. The visco-elastic characteristics of the skin no longer play a role during the lancing with the lancing system according to the invention.

The stationary positioning of the lancing depth reference element according to the invention does not require permanent fixation on the housing of the lancing device. Rather it is preferably moveable by means of a reference element drive. The reference element drive is preferably adapted so that the reference element is moved away from the skin, during at least a part of the return phase of the lancing movement of the needle element. Thereby optimum expression conditions are achieved.

In the context of the present invention it was established that it is advantageous to construct the lancing system so that two clearly differentiated states are guaranteed, namely a lancing state and an expression state:

In the lancing state optimum lancing conditions are established without compromise so that excellent reproducibility of the lancing depth is combined with a very minor pain is achieved. The lancing conditions are deliberately selected so that—in particular because of the prevailing relatively high compressive force—no expression takes place, i.e. no blood issues as yet.

Thereafter the lancing depth reference element is moved away from the skin which bulges into the housing opening (at least) to such an extent that the expression aid has an optimal effect.

The lancing depth reference element cannot only be moved after but also before lancing by means of the reference element drive. However, the movement is preferably completed before the skin is pressed against the housing skin contact surface, wherein a signal device can be provided by which it is indicated to the user that the lancing device is ready for pressing-on. Advantageous is a lancing system with a triggering lock which is adapted and arranged in such a manner that the lancing process of the needle element can only be triggered when the skin is in contact with the reference skin contact surface with a defined minimum contact pressure.

The lancing system according to the invention is in particular suitable for "one-step-andling". This means that the user has to place the lancing system on the finger only once while the system carries out a plurality of process steps such as for example creating the wound in the finger, expression of the blood from the finger and collecting of the blood after the lancing. The one-step handling systems in particular comprise:

Integrated systems which in addition to the lancing device, preferentially in the same housing, comprise an analytical unit with which an analyte in the issuing body fluid such as for example the glucose content in blood, can be determined.

Lancing systems with cannula-like needle elements, with which the needle is not completely pulled out of the skin after having reached the reversal point, but remains in the skin for a defined period of time. Such a system is described in European Patent Application EP 05027428.1 and International Patent Application PCT/EP 2006/001922. Therein a lancing system is also disclosed in which the desired lancing movement of the needle element is controlled by means of a control cam. The content of these applications is incorporated into the present application by way of reference.

Preferably, the system according to the invention has a needle element which comprises a capillary channel. Through said capillary channel blood can be collected following the lancing of the skin. Such a system will still be described in more detail.

In a preferred embodiment the lancing device can be used a plurality of times. It includes a holder by means of which a lancing unit can be interchangeably coupled with the lancet drive. Here, the reference skin contact surface of the lancing depth reference element is embodied on a disposable element which is intended for single use. The lancing unit can then consist of a needle element or lancet and a lancing depth reference element.

BRIEF DESCRIPTION OF THE DRAWINGS

Thereafter the invention is explained in more detail with reference to the preferred embodiments shown in the Figures. The special features shown therein can be used individually or in combination in order to create preferred embodiments of the invention. The described embodiments do not constitute any restriction of the generality of the subject matter defined in the claims. In the drawings:

FIG. 9 shows a lancing depth reference element embodied as shutter in three closure positions a to c;

FIG. 10 shows two closure positions of the shutter from FIG. 9 in lateral views a and b;

FIGS. 11a,b show an alternative lancing depth reference element with a plurality of components;

FIGS. 12a,b show a further embodiment of a lancing depth reference element;

FIGS. 13a,b show a further embodiment of the lancing depth reference element; and FIG. 14 shows an alternative embodiment of a lancing device with integrated analytical unit.

DESCRIPTION OF THE SELECTED EMBODIMENTS

The location-defining terms "front" and "rear" refer to the lancing direction. Thus the front end of the lancing system is the end at which the lancet or needle emerges from the lancing system upon movement in lancing direction.

Figure 1:
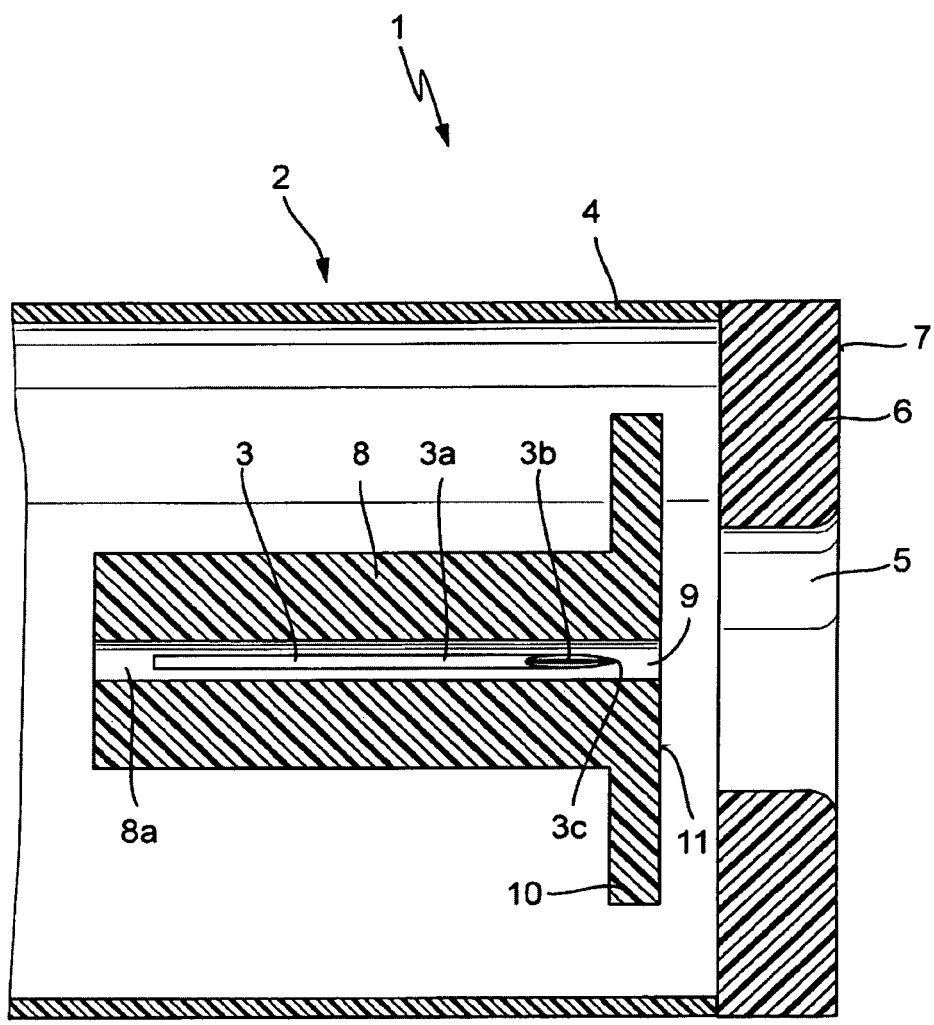
FIG. 1 shows a schematic sectional view of a part about a housing opening of a first embodiment of a lancing system.

FIGS. 1 and 2 schematically show the end located at the front in lancing direction of a lancing system 1 not shown in its entirety. The lancing system 1 comprises a likewise not completely shown lancing device 2 and a needle element 3. The lancing device 2 has a housing 4 with a housing opening 5 which is located in front wall 6 of the lancing device.

Regarding the minimum width of the housing opening 5 no sharp limit values which are correct for all applications can be provided since the expression-promoting effect depends on a plurality of factors. However, a minimum width of the housing opening 5, which (in the case of a circular opening) corresponds to a diameter of at least 4 mm, particularly preferable at least 6 mm, has proved to be advantageous in practice. Preferably the housing opening 5 is circular and has a diameter of 4 to 11 mm, preferably 6 to 8 mm. Even if it is not exactly circular its cross sectional area should correspond to the area of a circle with the mentioned diameter values. In any case, the opening is so large that the skin of a finger or other part of the body can bulge into the opening. During use a housing skin contact surface 7 surrounding the housing opening 5 is pressed against the skin of a body part.

The needle element 3 is embodied as a cannula 3a, comprising a capillary channel 3b. The front end is beveled in such a manner that a tip 3c is formed. Particularly preferably the needle element 3, designated as sampler, is manufactured of a flat sheet and comprises a capillary channel 3b, preferably a capillary channel open on one side, through which a body fluid, in particular blood, can be taken up from the skin.

The needle element 3 is precisely guided relative to a lancing depth reference element 8, for example as is shown in FIG. 1, in a guide channel 8a of the lancing depth reference element 8, which at the front, that is in lancing direction of the needle element 3, comprises an element opening 9. The element opening 9 is substantially smaller than the housing opening 5. In the example shown the lancing depth reference element 8 has two stops 10 at its front end. Evidently the stops 10 can also be embodied on another location of the reference element 8. A reference skin contact surface 11, which is adapted to contact the skin of the body part, is also arranged at the front end of the lancing depth reference element 8.

FIG. 1 shows the starting position of the lancing system 1 wherein the lancing depth reference element 8 is arranged in a rest position so that it is spaced from the edge of the housing 4. Before the lancing system 1 can be used the lancing depth reference element 8 is brought into its defined stationary position in which it also remains when the tip 3a of the needle element 3 passes in the forward phase of the lancing movement the reference skin contact surface 11 and emerges from the lancing depth reference element 8. This configuration designated as start position is illustrated in more detail in FIG. 2a.

FIGS. 2a to f show various positions of use of the lancing system 1. The sequence of the lancing movement in the individual phases is shown in the Figures. After the reversal point of the lancing movement has been reached the tip 3a of the needle 3 is retracted to a residual penetration depth or residual lancing depth. From here on the needle element 3 and the reference skin contact surface 11 simultaneously move away from the skin while maintaining the projection of the needle element 3 over the reference skin contact surface 11, thereby reducing the pressure on the skin in such a manner that blood can emerge. The capillary channel 3b of the needle element 3 takes up the blood. This movement phase is designated as collection phase.

In the start position of the lancing system 1 (FIG. 2a) the lancing depth reference element 8 is located in its defined stationary position with respect to the housing 4. The defined stationary position of the lancing depth reference element 8 can also be related to the housing skin contact surface 7. The stationary position is provided for example in that the lancing depth reference element 8 with its stop 10 contacts a corresponding housing stop 12 on the housing opening 5. The stationary position of the reference skin contact surface 11 is now unambiguously defined by the contact of the stop 10 with the housing stop 12. It is clear that the use of corresponding stops is only one possibility to locate the lancing depth reference element 8 in the defined stationary position. The lancing depth reference element 8 can also be moveably mounted wherein it may be biased towards the stop 12 by means of a spring. It is only important here that the stationary position is maintained in such a manner that the lancing depth of the needle element 3, which is set and determined by the lancing depth reference element 8, can be reliably guaranteed.

In the stationary position of the lancing depth reference element 8 the needle element 3 is arranged in such a manner that its tip 3c is located behind the reference skin contact surface 11. In the example shown the tip 3c is located approximately 3 to 4 mm behind the reference skin contact surface 11.

The lancing depth reference element 8 of the lancing system 1 is preferably located in its stationary position even before the lancing system 1 comes in contact with a body part 13, i.e. before the skin 14 of the finger 13 is pressed against the housing skin contact surface 7.

Figure 2A:
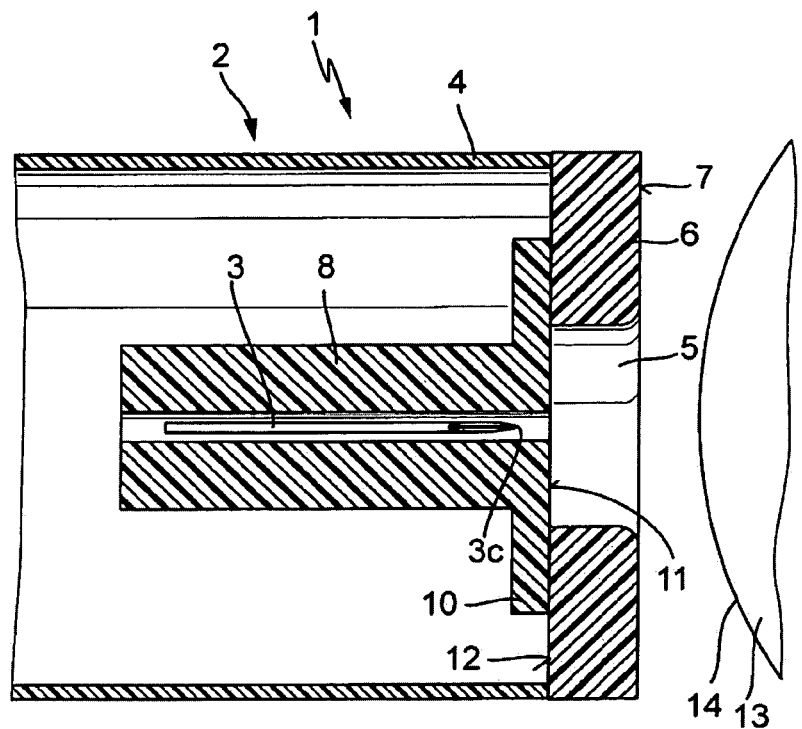
FIG. 2 shows a representation in seven positions of use a to g of the lancing system corresponding to FIG. 1.
Figure 2B:
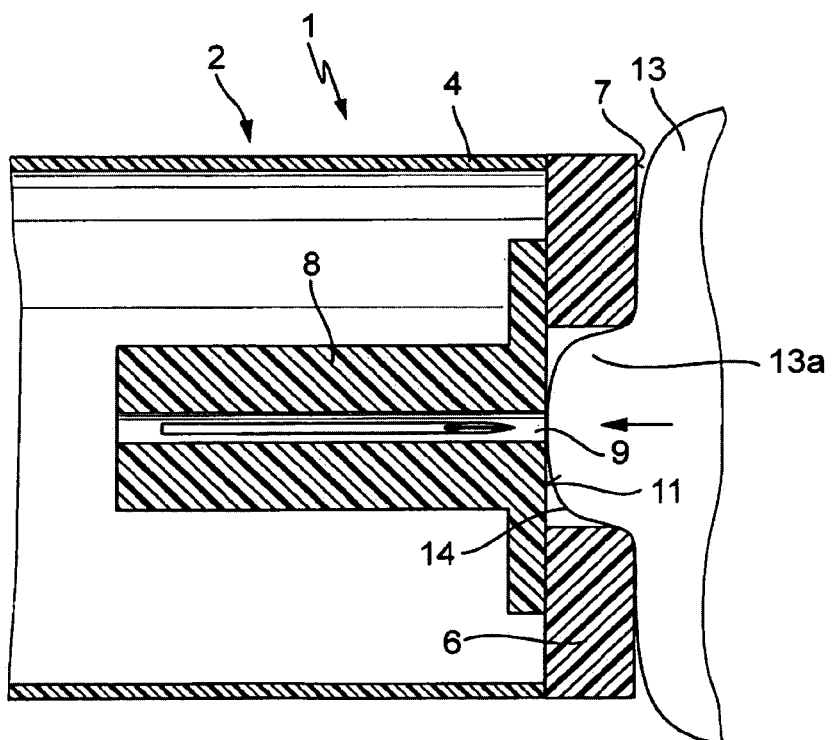

At the moment at which the lancing system 1 is pressed against the finger 13 the skin 14 of the finger bulges into the housing opening 5 of the lancing device 2 and presses against the reference skin contact surface 11, FIG. 2b. The skin 14 is thus in contact with both the reference skin contact surface 11 as well as the housing skin contact surface 7. The contact pressure of the skin against the housing skin contact surface 7 is within the range of approximately 5 to 10 N. The bulged-in skin presses against the reference skin contact surface 11 with approximately 3 N. This compressive force is maintained also with a lancing depth reference element 8 mounted in a spring-loaded manner.

Here, the object of the housing skin contact surface 7 is to squeeze the finger 13 in such a manner that the blood is pressed into the bulged-out part 13a of the finger 13. The reference skin contact surface 11 not only delimits the bulging-out of the finger 13 but additionally tautens the skin 14 in the region of the element opening 9 of the lancing depth reference element 8. Thus, in the lancing system according to the invention, on the one hand the blood is pressed into the region of the body part in which a wound is to be created, while on the other hand the denting of the skin typically caused upon entering of the needle is prevented in this region by the tautening of the skin.

Figure 2C:
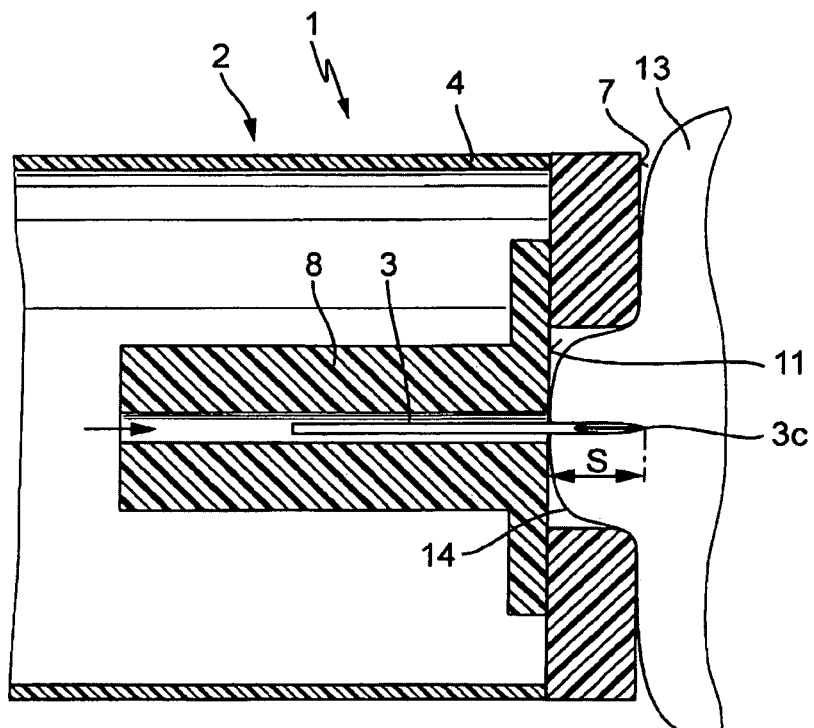

Once the lancing system 1 contacts the finger 13, the lancing can be triggered. The needle element 3 then moves in lancing direction and penetrates the skin 14 of the finger 13 with its tip 3c as shown in FIG. 2c. In the process, the tip 3c protrudes into the skin 14 by the preset lancing depth S of approximately 1.5 to 2.5 mm. This position defined as reversal point is reached after approximately 1 msec.

Figure 2D:
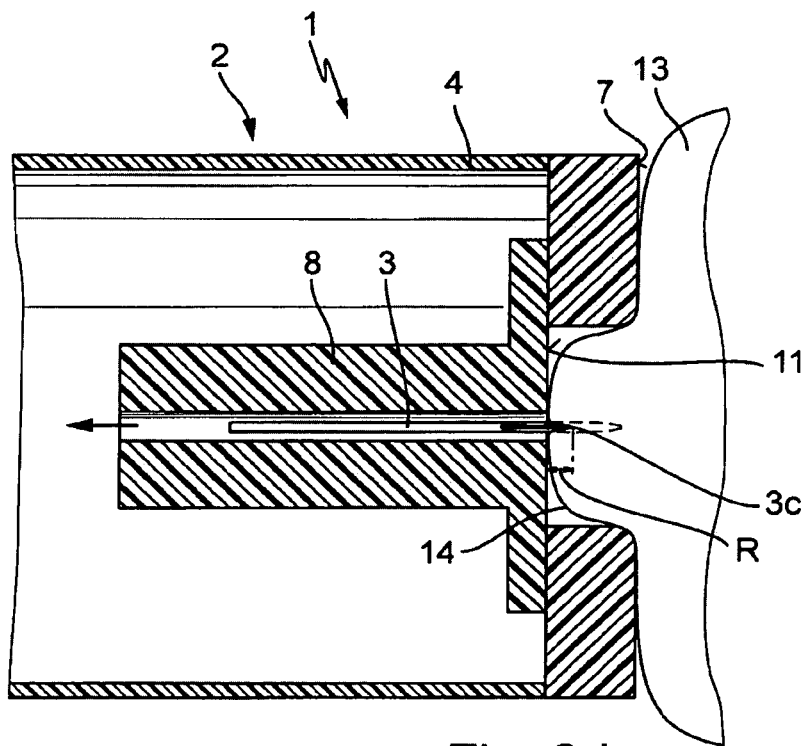

Thereafter the needle element 3 is moved opposite to the lancing direction until its tip 3c is retracted to a defined residual lancing depth R, which amounts to approximately 0.5 mm and which is reached after approximately 2 msec. The lancing depth reference element 8 remains in its stationary position with its reference skin contact surface 11 and continues to contact the skin 14. The part-sections of the lancing movement which occur up to this point, i.e. the lancing up to the reaching of the reversal point of the lancing movement at the lancing depth S and the retraction of the needle element 3 to the residual lancing depth R are preferably substantially faster than the following part-sections of the return phase of the lancing movement. During this rapid movement (in the millisecond range), in particular during the first part-section of the return phase, the reference skin contact surface 11 preferably remains positioned in its stationary position (FIG. 2d).

Figure 2E:
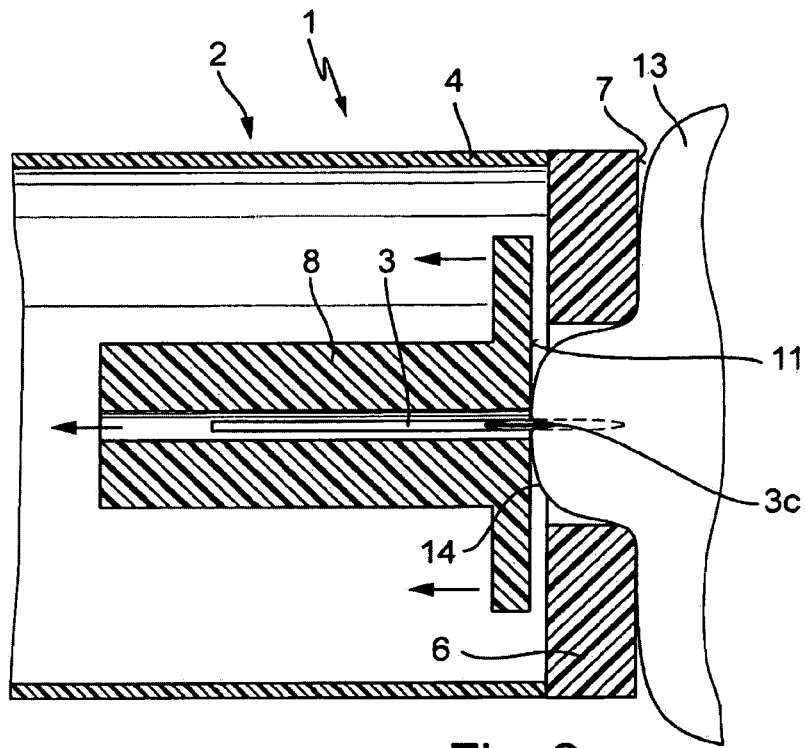
Figure 2F:
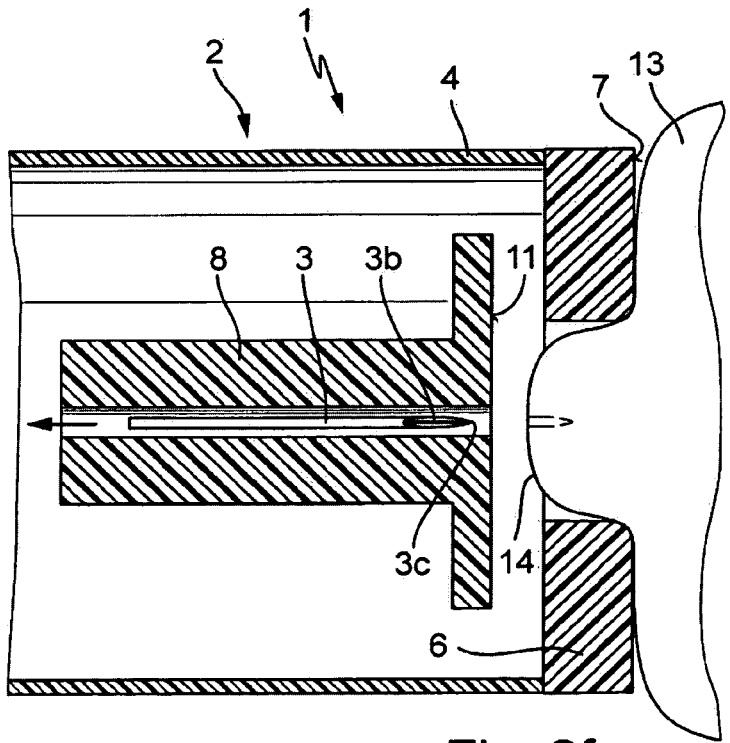
Figure 2G:
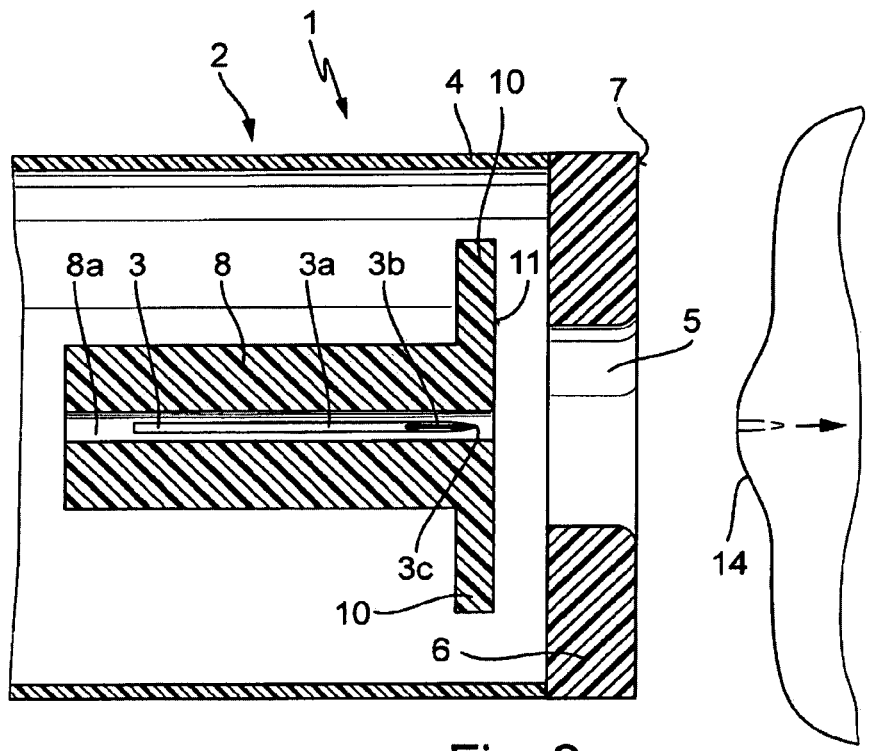

In the following part-section of the return phase, FIG. 2e, the lancing depth reference element 8 is moved opposite to the lancing direction. During this part of the return phase the lancing depth reference element 8 is preferentially moved simultaneously with the needle element 3. This movement can take place with different speeds.

In an advantageous embodiment however the lancing depth reference element 8 and the needle element 3 are on this part of the return phase moved synchronously so that the relative position between the tip 3c of the needle element 3 and the reference skin contact surface 11 of the lancing depth reference element 8 remain unchanged. Thus the residual lancing depth R is maintained while the lancing depth reference element 8 is moved away from the skin 14. This leads to a relaxation of the skin which follows the lancing depth reference element 8 because of its viscoelasticity. The pressure of the lancing depth reference element 8 on the skin 14 in the region surrounding the lancing site is reduced however, so that blood flow from the wound is made possible.

Preferentially the lancing depth reference element 8 is thus moved from its stationary position, relative to the housing skin contact surface 7, in such a manner that the reference skin contact surface 11 remains in contact with the skin 14. This movement takes place before the tip 3c of the needle element 3 is completely pulled out of the skin 14.

When the tip 3c of the needle element 3 has reliably left the skin 14, after approximately 0.5 to 3 sec, the needle element 3 is retracted so far that the tip 3c is located behind the reference skin contact surface 11 of the lancing depth reference element 8. The needle element 3 and the lancing depth reference element 8, which likewise was moved opposite to the lancing direction so far that the skin 14 is no longer in contact with the reference skin contact surface 11, have then reached their rest position. The sample gained with the capillary channel 3b can now be transported to a chemical test unit for example to a sample carrier. In particular, the blood may flow from the capillary channel 3b of the needle element 3 onto a test carrier which is not shown.

Thereafter, the lancing system 1 is removed from the skin 14. The skin no longer has any contact with the housing contact surface 7 as is evident from FIG. 2g. This completes the lancing process.

Alternatively, the needle element 3 can also be embodied without capillary channel 3b. The lancing depth reference element 8 is then moved away from the housing opening 5 so far that an analytical unit with an analytical element can be moved against the housing opening 5 in order to collect the blood issuing from the wound in the skin. In this case the movement sequence of the lancing movement is very different. The lancing movement merely comprises a fast forward phase up to the reaching of the reversal point and a fast return phase until the needle element 3 has left from the skin. The lancing depth reference element 8 is subsequently moved away from the housing opening 5 until it is no longer in contact with the skin and adequate space is available in the lancing device 2 so that an analytical element can be placed against the skin in order to take up the emerging blood.

Figure 3:
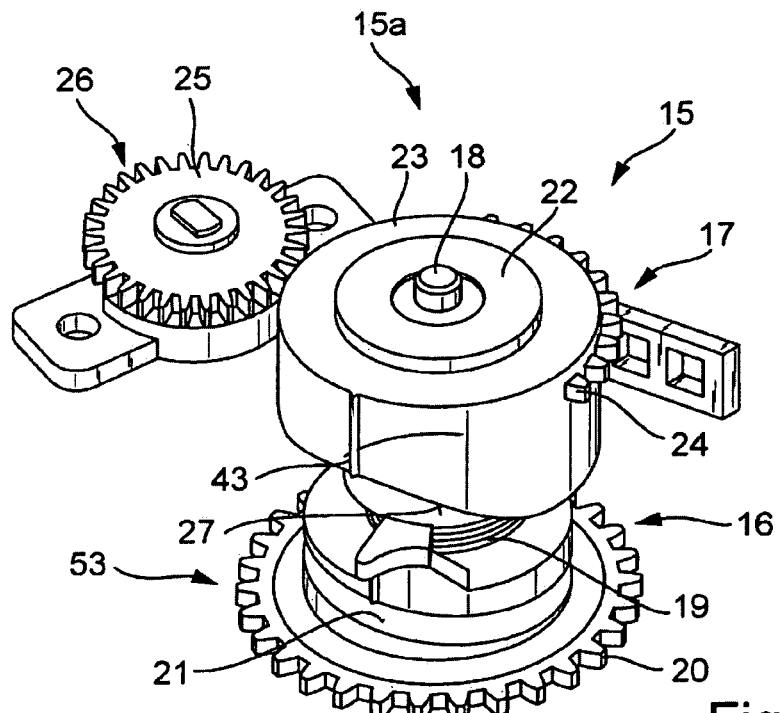
FIG. 3 shows a drive unit comprising tensioning rotor and drive rotor.

In order to realize the lancing movement with collection phase described in FIG. 2 to take up the emerging blood, various drive concepts are known in the prior art. A likewise suitable concept is shown in FIG. 3. It comprises a lancet drive 15a embodied as drive unit 15 comprising a tensioning rotor 16, a drive rotor 17 and a drive spring 19 as well as a motor (which is not shown here). The two rotors are mounted on an axle 18. The drive spring 19 arranged between the rotors serves for the transmission of force and torque from the tensioning rotor 16 to the drive rotor 17. The tensioning rotor 16 shown in FIG. 3 has drive teeth 20 by which it can be driven by the motor of the drive unit 15.

The rotors of the drive unit 15 are only moved in one direction so that after a 360° revolution the rotors 16, 17 are again arranged in their starting position. Rotating back in the opposite direction is not necessary. Drive units of this type are designated as OWADAC drives. An example of such a drive is known from EP 1504718. The drive unit described there is likewise suitable for providing the lancing movement according to FIG. 2.

Figure 4:
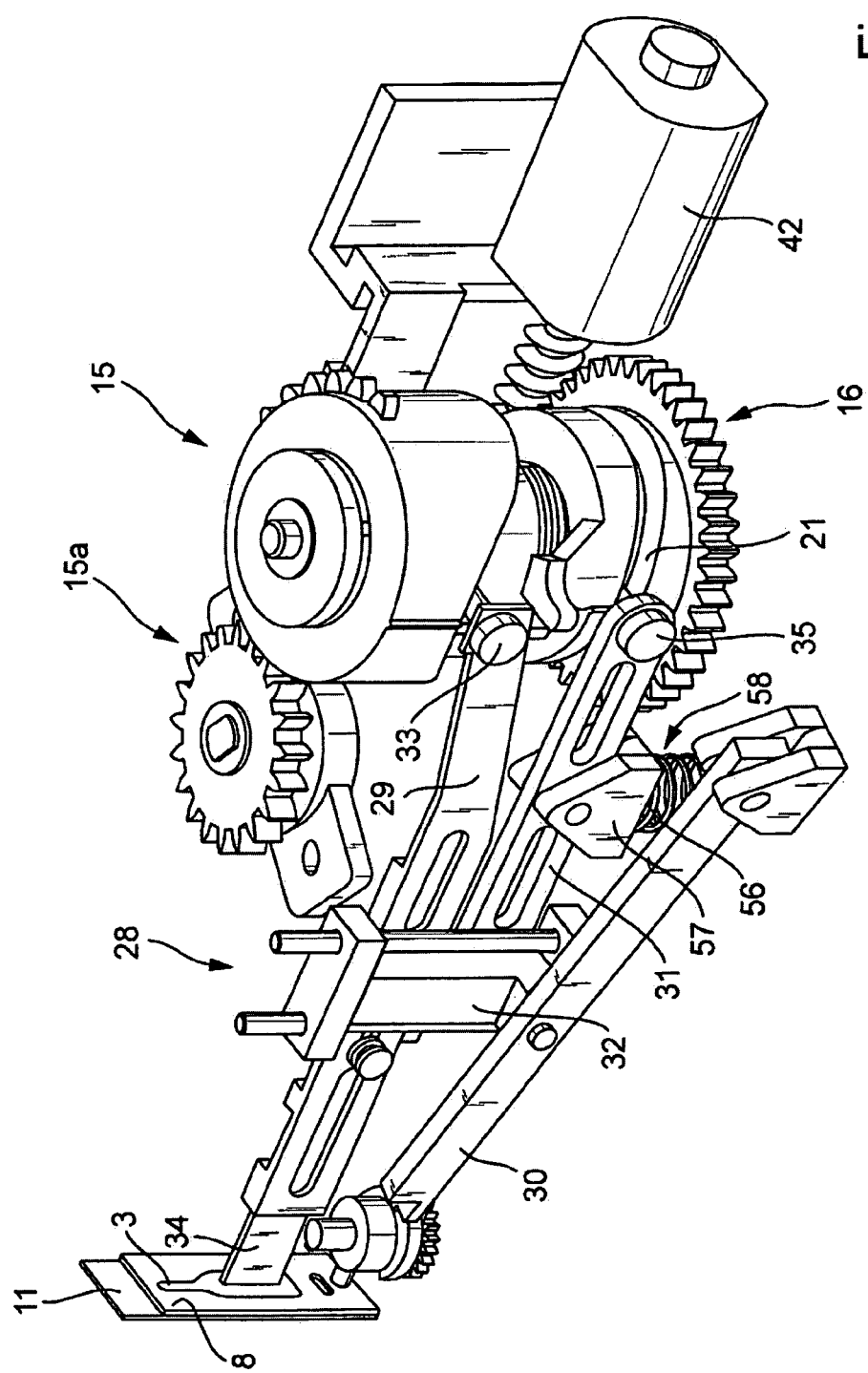
FIG. 4 shows a perspective view of a drive mechanical system with a drive unit, a coupling mechanism and a lancing unit.
Figure 5:
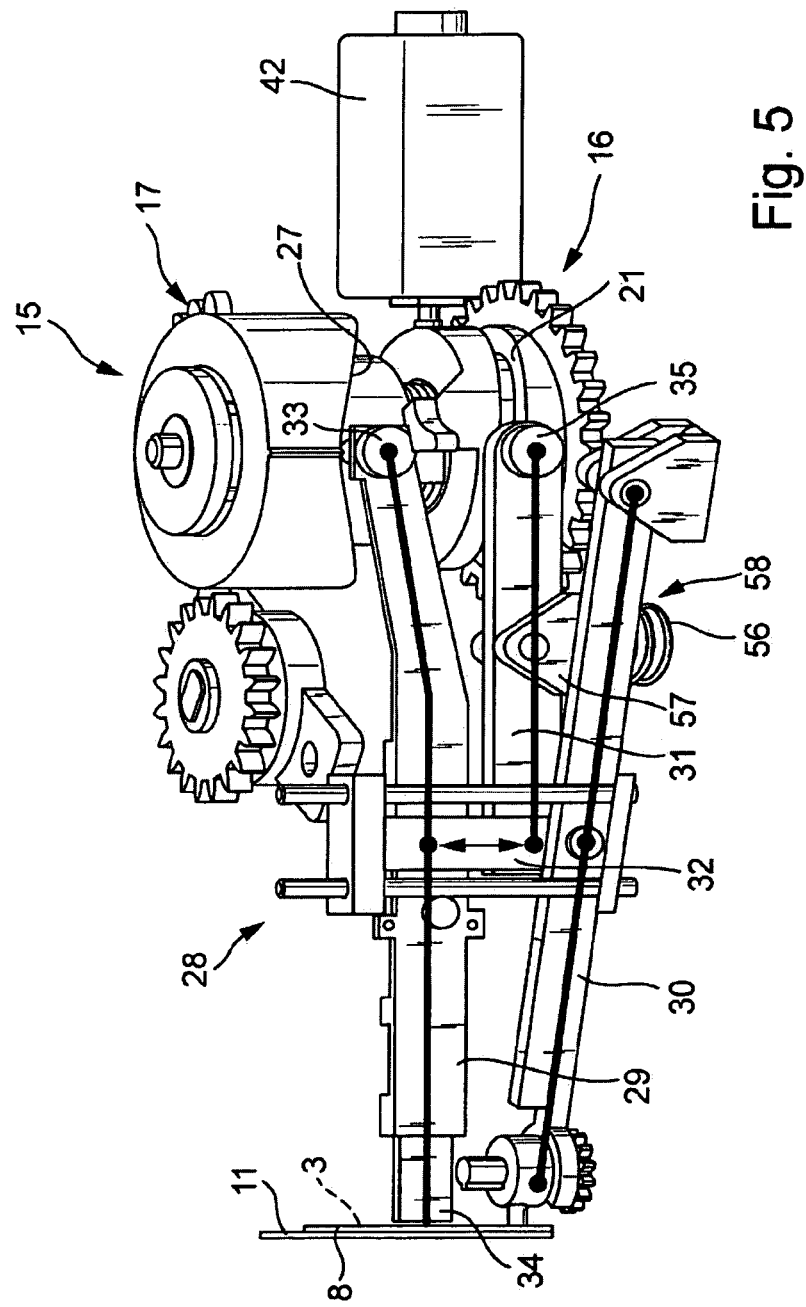
FIG. 5 shows a further perspective view of the drive unit from FIG. 4.

A reference control curve 21 arranged on the tensioning rotor 16 controls the lancing depth reference element 8 of the lancing system by way of a coupling mechanism which is not shown here. The reference control curve 21 is preferably a narrow groove in which a traveler 35 shown in FIGS. 4 and 5 is positively guided. The control curve however can also be a control cam embodied as control edge or slot open on one side. Therein a traveler can run, subject to spring load, without positive guidance of the traveler.

The tensioning rotor 16 with the reference control curve 21 is part of a reference element drive 53. The drive also comprises the drive rotor 17, the drive spring 18 as well as a reference element lever 30 described in more detail in connection with FIGS. 4 and 5. The lancing depth reference element is moved by means of the reference element drive 53. The reference element drive 53 is independent of the drive of the needle element 3. However, they can be at least partially coupled to each other and also possess common components as is illustrated in FIG. 4. For example the drive spring 19 in the present example is a common component of the two drives. The reference element drive 53 however can also be electrically, electronically or electromechanically separated from the drive of the needle element; purely mechanical separations are also possible.

The drive rotor 17 of the drive unit 15 is embodied in two parts, wherein an inner adjusting part 22 is axially adjustable relative to an outer rotor part 23. By adjusting the two parts relative to each other the lancing depth of the needle element 3 is defined and set relative to the lancing depth reference element 8. A lancing control curve 43 which determines a part of the lancing travel of the needle element including the reversal point of the lancing movement, is partially covered relative to the rotor part 23 depending on the position of the adjusting part 22. The two-part embodiment of the drive rotor 17 also results in a two-part control cam which is formed by the lancing control curve 43 and the lancet control curve 27. Since the two-part control cam is changeable in its shape, it cannot be embodied as closed, positively guided path. Rather, the traveler 33 on the lancet lever 29, which is guided in the two-part control cam, is forced by a spring force (which is not shown) to follow the control edge of the control cam.

The rotor part 23 of the drive rotor 17 comprises teeth 24 on a part of an outer circumference. Teeth 24 intermesh with a damper 26, embodied as gear 25, during a part of the rotary movement so that the movement of the drive rotor 17 is slowed down by the damper 26.

The rotor part 23 is shaped at its lower side (oriented towards the tensioning rotor 16) in form of a lancet control curve 27, thereby controlling the movement of the needle element via a coupling mechanism.

FIGS. 4 and 5 each show a perspective view of a mechanical drive system in which the drive unit 15 from FIG. 3 is integrated. A coupling mechanism 28 comprises a lancet lever 29, a reference element lever 30 and a coupling lever 31 as well as a bearing block 32. The lancet lever 29, the reference element lever 30 and the coupling lever 31 are coupled together via the bearing block 32. Axial displacement of the bearing block 32, caused by one of the levers 15, is at least partially or for limited time transmitted to the other levers so that a simultaneous movement of the needle element 3 and the lancing depth reference element 8 is achieved. By means of the coupling mechanism 28 rotary movements of the drive unit 15 are transmitted to the lancing unit comprising needle element 3 and lancing depth reference element 8, with reference skin contact surface 11.

A traveler 33, which is arranged and fastened at an end of the lancet lever 29, travels along the lancet control curve 27 and the lancing control curve 43 of the drive rotor 17. The movement of the traveler 33 is transmitted via the lancet lever 29 to the lancet and the needle element 3 respectively. It is fastened to the lancet lever 29 by means of a coupling element 34. In this manner various needle elements or lancets can be connected with the lancing device. In particular with one-way lancets such a coupling element 34 is necessary to allow plural use of the lancing device.

The coupling lever 31 is moved via a traveler 35 which is guided along the reference control curve 21 of the tensioning rotor 16. The coupling lever 31 is fastened to the bearing block 32 so that a movement of the coupling lever 31 caused by traveling along the reference control curve 21 causes an axial displacement of the bearing block 32 in and opposite to the lancing direction. The axial movement of the bearing block 32 causes a movement of the lancing depth reference element 8 coupled with the reference element lever 30.

By combining the various levers of the coupling mechanism 28 with the bearing block 32 it is possible to move the needle element 3 jointly with the lancing depth reference element 8 during a part of the return phase of the lancing movement in such a manner that the desired residual lancing depth remains constant.

This arrangement likewise makes it possible to let the reference skin contact surface 11 resiliently give way relative to the housing 4 under a skin pressure force preferentially amounting to approx. 3 N without the lancing depth and/or the residual lancing depth (collecting depth) being affected in the collecting phase.

The coupling lever 31 which connects the traveler 35 and the bearing block 32 is rotatably mounted in a bearing 57. The bearing 57 is held by a spring device 58 embodied as spring 56. For example the spring 56 can be configured as a metal spring. This produces a resilient mounting of the bearing block 32 and thus ultimately a resilient mounting of the lancing depth reference element 8 with the reference skin contact surface 11 arranged at its upper end.

The lancing depth reference element 8 is mounted moveably opposite to the lancing direction of the needle element 3. The spring 56 pushes the bearing 57 in the lancing direction by its preload. The movement of the bearing 57 in lancing direction or the movement of the coupling mechanism 28 in lancing direction can be limited by a stop. It is also possible to limit the lancing depth reference element 8 itself by a stop so that the spring driven movement distance caused by the spring 56 is limited.

When the skin is pressed against the reference skin contact surface 11 the lancing depth reference element 8 is displaced to the rear opposite to the lancing direction against the force of the spring 56, while the spring 56 is compressed. The compressive force acting on the skin then corresponds to the spring force of the spring device 58. This allows a limitation of the maximum permissible pressure on the skin.

FIGS. 4 and 5 furthermore show that the lancing depth reference element 8 and the needle element 3 can each be disposable elements. Preferably they are jointly replaced, whereas the lancet drive 15 and the coupling mechanism 28 are reusable.

FIGS. 4 and 5 show a lancing depth reference element 8 without an element opening 9. It can for example be a substantially plane element which can simultaneously fulfill the function of an analytical element and whose upper edge forms the reference skin contact surface 11. The needle element 3 is then moved along the lancing depth reference element 8 during the lancing movement and passes the reference skin contact surface 11. The minimum distance, i.e. the smallest distance between the reference skin contact surface 11 and the needle element 3, should be at most 1 mm, preferably at most 0.5 mm. By this relatively small distance it is ensured that the needle element 3 lances a region of the skin which is tautened by the reference skin contact surface 11.

The movement sequence of the drive unit 15 for realizing the lancing movement described in FIG. 2 is shown in detail in the FIGS. 6a to 6i. Here, various positions of the tensioning rotor 16 relative to the drive rotor 17 are shown.

Figure 7A:
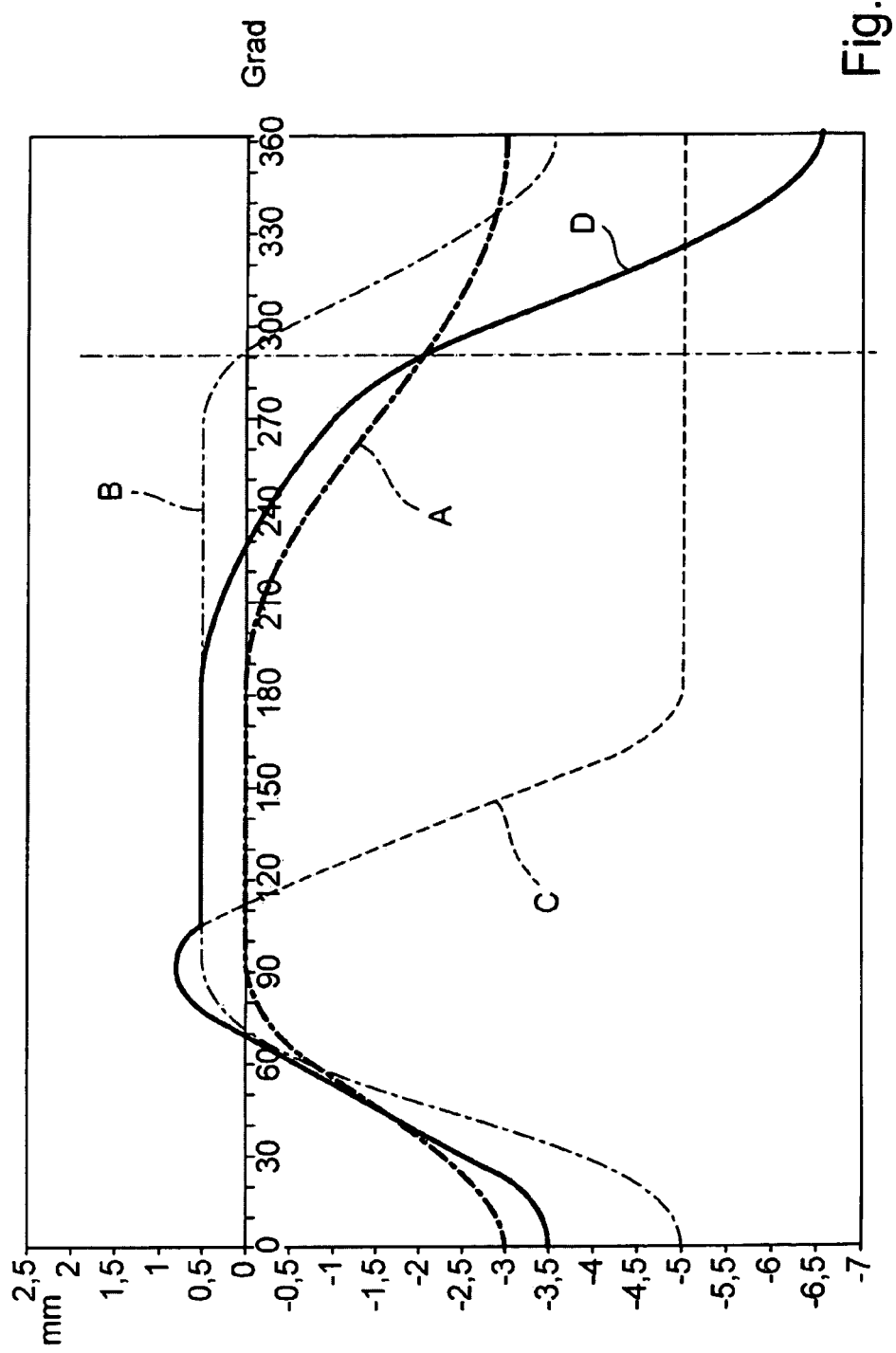
FIG. 7 shows the resulting control curves of the drive mechanical system as well as the resulting curve of the needle element over a 360° rotation.
Figure 7B:
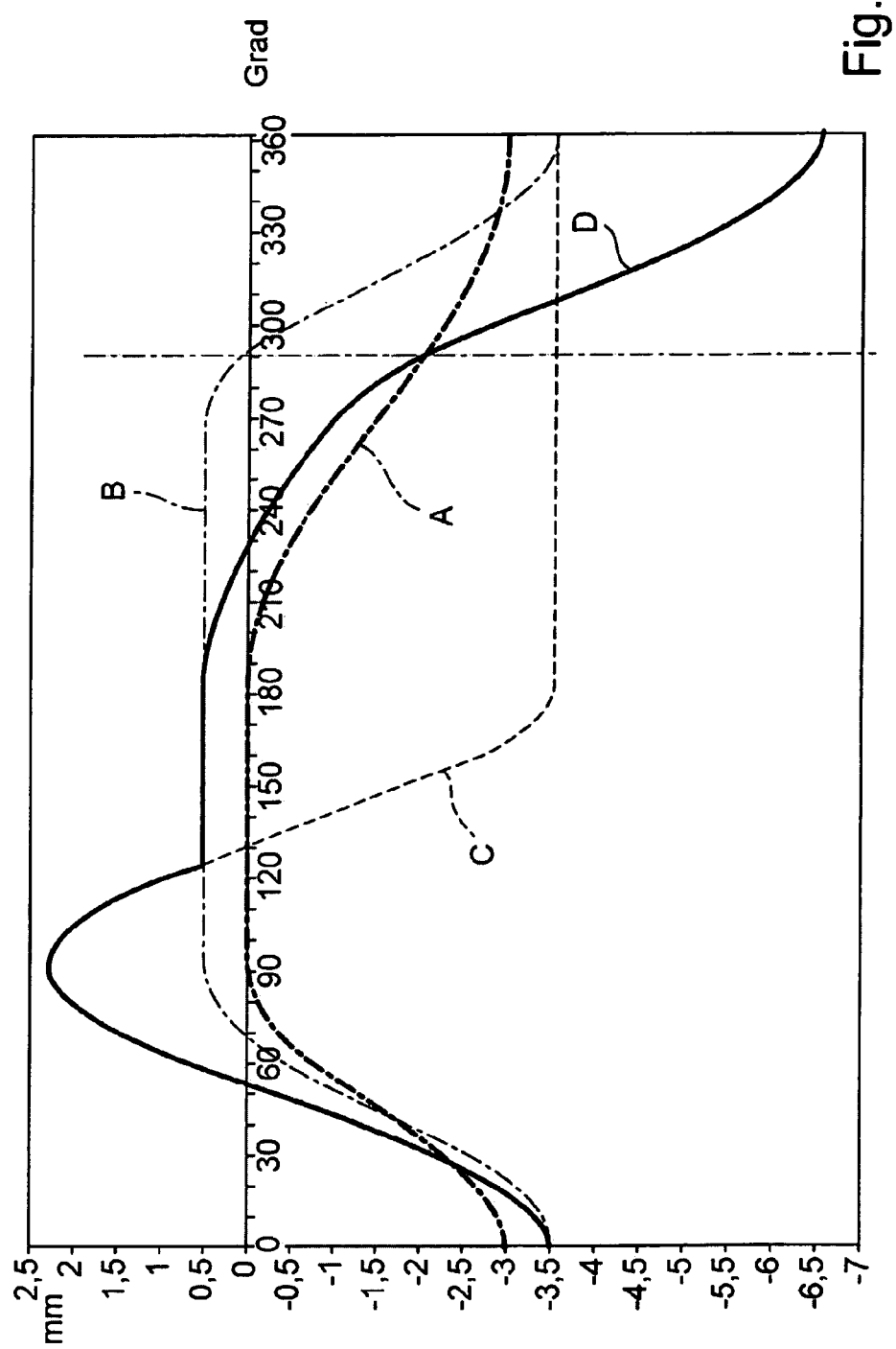

The various angle positions of the two rotors over a 360° revolution are illustrated in graphical form by FIGS. 7a and 7b, wherein the rotation angles of the rotors are plotted in degrees over the X-axis. FIGS. 7a and 7b show a geometrical representation of the strokes of the end of the lancet lever 29 and of the reference element lever 30 connected with the lancing unit, these strokes being caused by the control curves of the tensioning rotor 16 and the drive rotor 17. Curve A shows the stroke of the reference element lever 30, which corresponds to the position of the lancing depth reference element 8. Curve B shows the stroke caused by the lancet control curve 27. Curve C shows the stroke caused by the lancing control curve 43. Curve D is the resultant curve (which represents the stroke, i.e. the lancing movement, of the needle element 3).

Figure 6A:
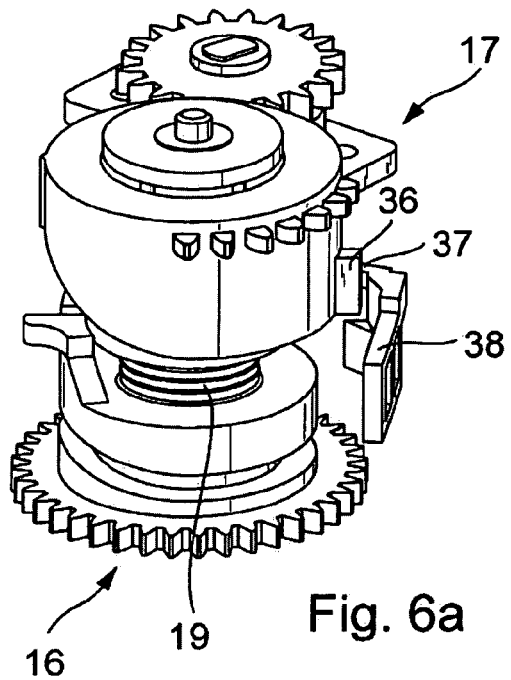
FIG. 6 shows a representation of the positions a to i of the drive unit corresponding to FIG. 2.

FIG. 6a shows the starting position of the two rotors 16, 17 which is designated with 0°. The drive rotor 17 contacts, by means of a holding protrusion 36, an engagement pin 37 of an engagement device 38 so that the movement of the drive rotor 17 is locked in the direction of the arrow, i.e. in anticlockwise direction.

Figure 6B:
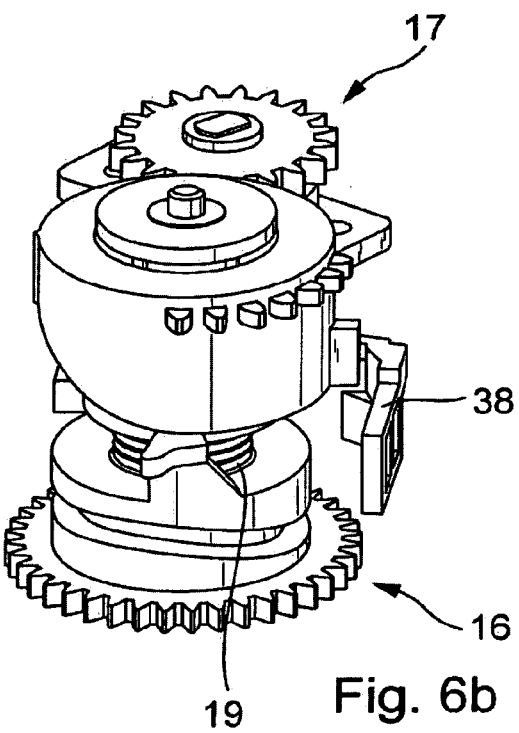
Figure 6C:
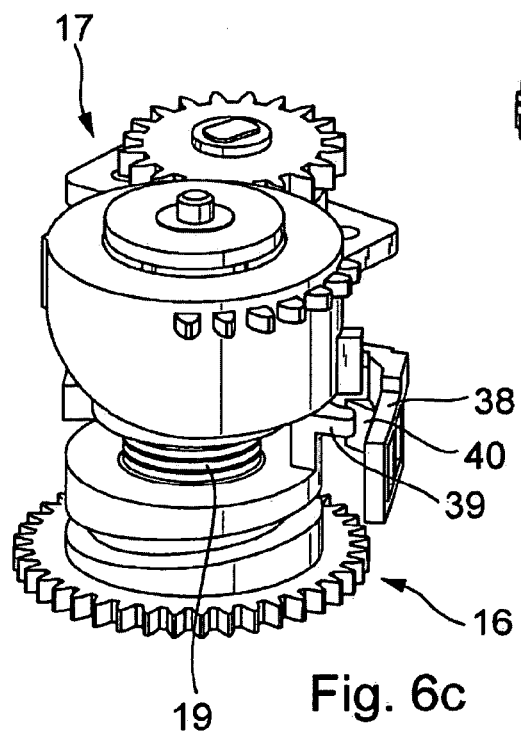

The tensioning rotor 16 is now rotated in anti-clockwise direction by a drive motor 42 shown in FIGS. 4 and 5. In this process, the drive spring 19 between the tensioning rotor 16 and the drive rotor 17 is slowly tensioned beyond its pretension (FIG. 6b). At the same time, the lancing depth reference element 8 coupled via the coupling mechanism 28 is moved into its defined stationary position (see FIG. 2a). The needle element 3 is jointly moved with the lancing depth reference element 8 so that their relative position remains constant. Approximately after a 90° rotation of the tensioning rotor 16 (curve A, FIGS. 7a,b) the lancing depth reference element 8 has reached its defined stationary position.

Figure 6D:
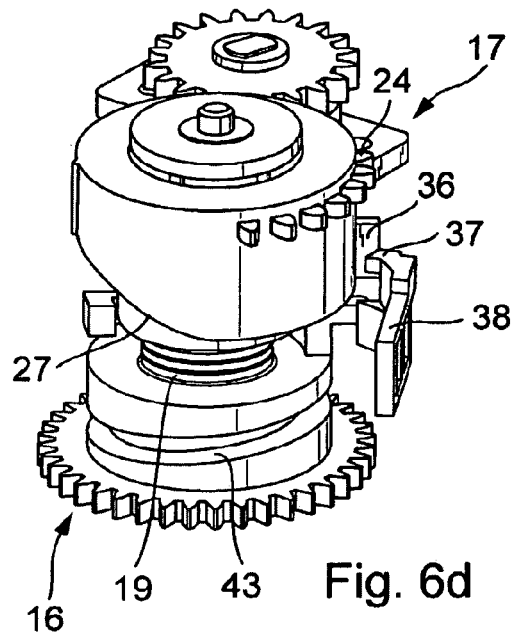
Figure 6E:
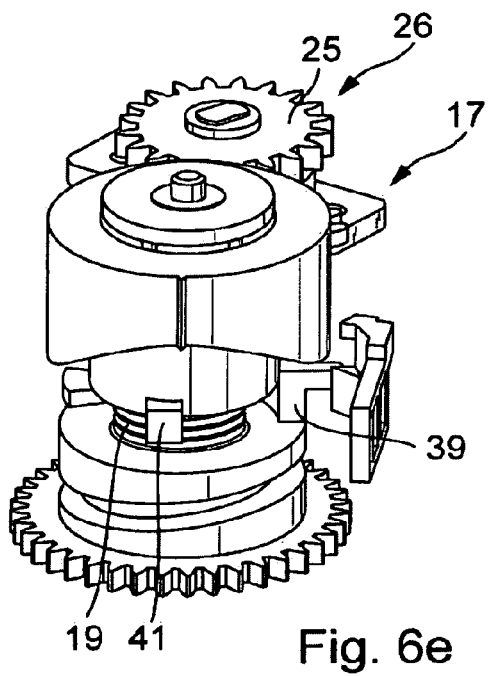
Figure 6F:
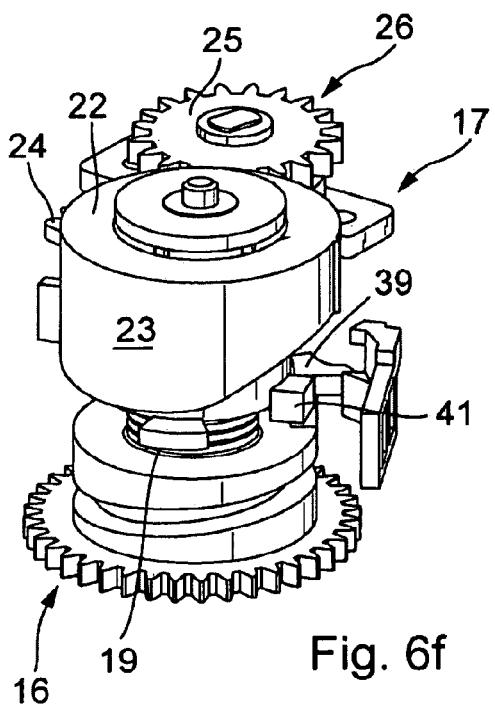

By additional rotating of the tensioning rotor 16 in anticlockwise direction the drive spring 19 is completely tensioned. Upon reaching of the 180° position shown in FIG. 6c a triggering cam 39 of the tensioning rotor 16 presses against a triggering hook 40 of the moveable engagement device 38 which is thereby swiveled. The drive rotor 17 is released and the drive spring 19 relaxes very fast. Lancing is triggered and the lancing movement of the needle element 3 starts (FIG. 6d). The tensioning rotor 16 remains in its position while the drive rotor 17 is rotated at very high speed in anticlockwise direction.

The rotary movement of the drive rotor 17 is transmitted to the lancet lever 29 moved by the lancet control curve 27 so that the needle element 3 is driven by the relaxing of the drive spring 19. In accordance with the lancet control curve 27 and the lancing control curve 43 the needle element 3 is now guided in a rapid movement in lancing direction until the reversal point is reached and subsequently retracted to the residual lancing depth R. The reversal point of the lancing movement is approximately reached with a rotation of the drive rotor 17 of 90°.

Between the 90° position of the drive rotor 17 (FIG. 6e) and the 180° position (FIG. 6f) the teeth 24 of the drive rotor 17 engage in the gear 25 of the damper 26 as a result of which the movement speed of the drive rotor 17 is slowed down so that the rotary movement of the drive rotor 17 relative to the tensioning rotor 16 is stopped in a dampened manner. The needle element 3 has now reached the residual lancing depth R which preferentially amounts to approximately 0.5 mm.

At the rotary position of the drive rotor 17 of 180° (FIG. 6f) (up to for instance an inner cam ring of the inner adjusting part 22) a protrusion 41 of the drive rotor 17 strikes the triggering cam 39 of the tensioning rotor 16. This causes the tensioning rotor 16 and the drive rotor 17 to be coupled together and jointly moved by the pretension of the drive spring 19.

Figure 6G:
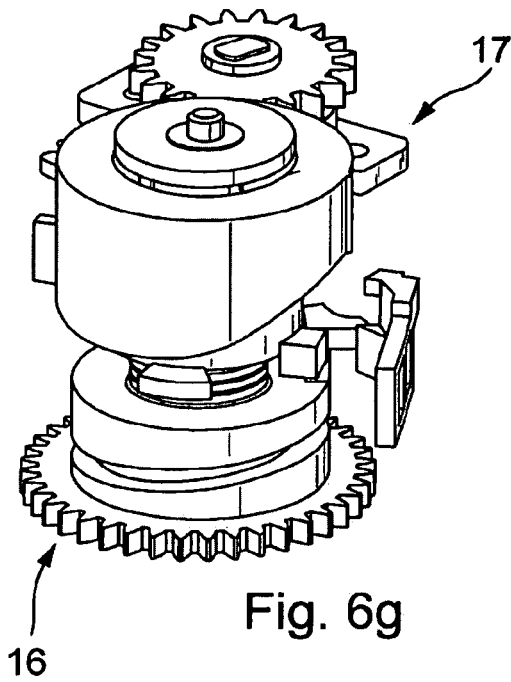

During the common movement of the two rotors between 180° and approximately 270° the relative distance between the needle element 3 and the lancing depth reference element 8 remains constant. The common movement of the lancing unit is characterized by the parallel curves A and D in FIG. 7a,b. This section is the collection phase in which the needle remains at the residual lancing depth R and is simultaneously retracted in synchronization with the lancing depth reference element 8 as is also shown in FIG. 2e. The position of the rotors during the collection process is shown in FIG. 6g.

Figure 6H:
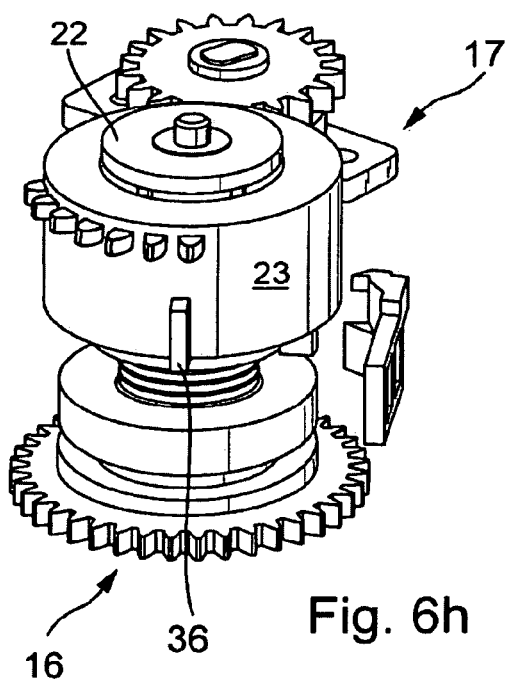
Figure 6I:
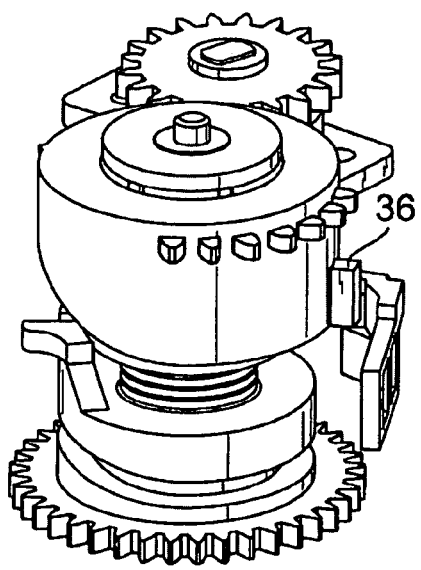

FIG. 6h then shows the rotary position of approximately 270° at which the retraction of the needle element 3 into the lancing depth reference element 8 starts. The curve D of the needle element from FIG. 7 approaches the curve A of the lancing depth reference element 8 and finally intersects it at approximately 290°. At that point the needle element 3 is retracted into the lancing depth reference element 8. Both are now moved back into their rest positions which is reached at a rotor position of 360° (FIG. 6i).

The two FIGS. 7a and 7b differ by a differently set lancing depth. FIG. 7a shows the lancing depth set at the minimum, FIG. 7b the lancing depth set at the maximum. Curve C from FIG. 7b is shifted relative to curve C from FIG. 7a. This shift results from an axial displacement of the adjusting part 22 relative to the rotor part 23 which is shown in detail in FIGS. 8a to 8d. These show the rotors upside down, so that the position in space corresponds to the remaining Figures. The minimum lancing depth is to approximately 0.75 mm, the maximum lancing depth 15 approximately 2.3 mm.

When the tensioning rotor 16 is moved first until it has reached its rotary position of 180° the lancing depth reference element 8 is lifted by 3 mm during the movement. At the same time, the needle element is also lifted by this stroke of 3 mm.

The movement curve of the needle element 3 (curve D) resulting after the triggering of the lancing, i.e. from the moment at which the drive rotor 17 moves, corresponds firstly to the curve B until at a later rotary angle the axially adjustable curve C takes the lead and determines the course of curve D. From this rotary angle the traveler 33 follows the lancing control curve 43 of the adjusting part 22. From the point at which curve C again falls below the curve B, curve B leads again, i.e. the lancet control curve 27 again takes over the guidance of the traveler 33.

With minimum lancing depth setting (FIG. 7a) these transfer points between the curves B and C are located at approximately 70° rotary angle of the drive rotor 17 (from curve B to curve C) and at approximately 105° rotary angle (curve C to curve B). With maximum lancing depth (FIG. 7b) curve C already leads from 0° rotary angle and hands over the lead to curve B at approximately 120°.

On reaching the 180° position of drive rotor 17, drive rotor 17 and tensioning rotor 16 are coupled together. Both rotors move in parallel. Traveler 35 is now guided in the reference control curve 21 causing the bearing block 32 to be moved down. Thus, the free end of lancet lever 29, in which coupling element 34 is arranged, is also guided downward. By this superimposition of the lever movements it is possible to move the needle element 3 synchronously and parallel to the lancing depth reference element 8 so that their relative distance, which corresponds to the residual lancing depth, remains constant. This is illustrated by the parallel course of the curves A and D in this section of the rotation.

From a rotary movement of 270° the lancet control curve 27 influences the traveler 33 in such a manner that the needle element 3 now again follows the control cam B in parallel. In other words, the needle element 3 is moved back relative to the lancing depth reference element 8 until it is retracted into the lancing depth reference element 8.

Figure 8A:
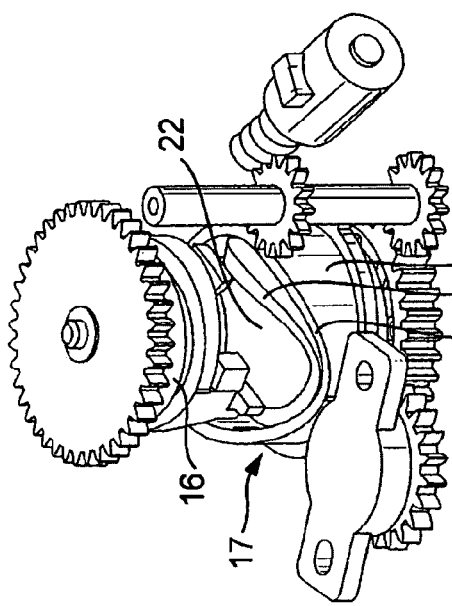
FIG. 8 shows the drive unit with set minimum and maximum lancing depth of the needle elements.
Figure 8B:
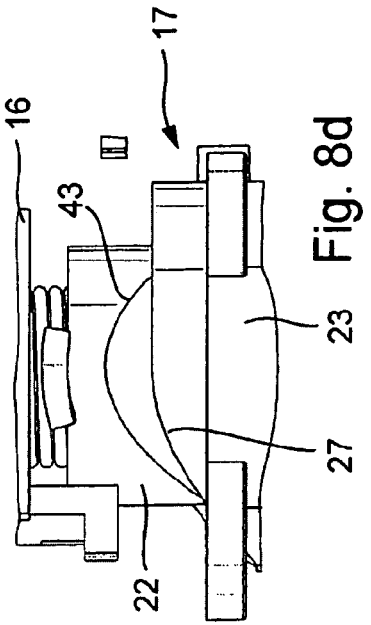

FIGS. 8*a* and 8*b* show (from the below) the drive unit 15 rotated by 180° in various positions of the adjusting part 22 relative to the rotor part 23 of the drive rotor 17. FIG. 8*a* shows the setting of the minimum lancing depth. The adjusting part 22 is axially shifted downwards relative to the rotor part 23, i.e. away from the tensioning rotor 16.

Figure 8C:
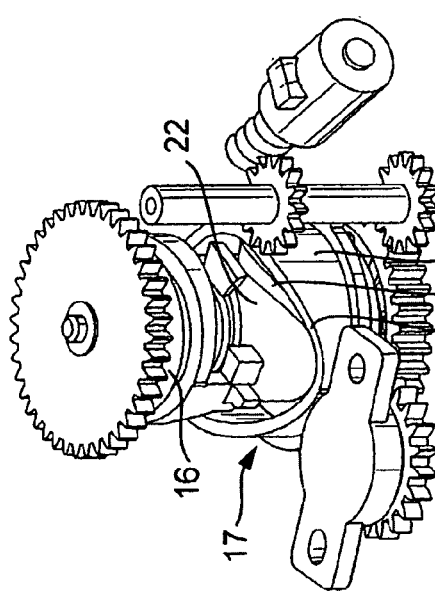

FIG. 8*c*, which represents a lateral view of the drive with setting of the minimum lancing depth, shows the lancet control curve 27 as well as the lancing control curve 43, both being responsible for the movement of the needle element. The control curve 43 protrudes only slightly over the lancet control curve, so that the corresponding penetration of the needle or lancet into the skin is also small.

Figure 8D:
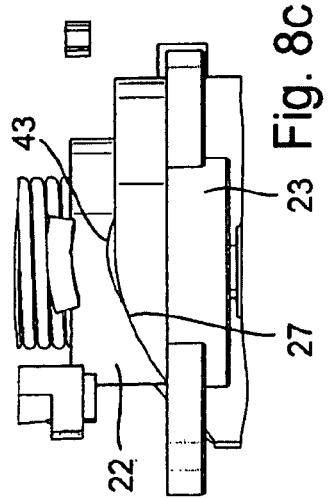

FIGS. 8*b* and 8*d* show the drive unit 15 with maximum setting of the lancing depth. The adjusting part 22 is axially shifted relative to the rotor part 23 in the direction of the tensioning rotor 16. The traveler for controlling the movement of the lancet is guided by the control curve 43 which is clearly higher than the lancet control curve 27. This results in a large lancing depth. The control curve 43 determines the movement of the needle element 3 during the entire forward phase and the rapid part of the return phase.

FIG. 9 shows a lancing depth reference element 8 which is embodied with a two-part shutter 44 defining an element opening 9. In the forward phase of the lancing movement tip 3*c* of needle element 3 passes through the element opening 9 of the lancing depth reference element 8 which is another preferred embodiment. The element opening 9 is advantageously variable in its size. It can also be reduced so far that the lancing depth reference element 8 is closed.

The element opening 9 of the lancing depth reference element 8 is dimensioned so that skin which is in contact with the reference skin contact surface 11 is tautened. The minimum distance between the reference skin contact surface 11 and the needle element 3 is generally at most 1.5 mm, preferably at most 1 mm, particularly preferably at most 0.5 mm, as has already been described supra for a lancing depth reference element without element opening. In case of lancing depth reference elements 8 with an element opening 9 this smallest distance between the reference skin contact surface 11 and the needle element 3 defines a corresponding opening cross section. The cross section of the element opening 9 is dimensioned so that in case of a circular opening, the cross section corresponds to a maximum diameter of 3 mm, particularly preferable a maximum of 2 mm. Non-circular element openings 9 have a corresponding cross section. Possible cross sectional shapes of preferred element openings are quadrilateral or polygonal cross sections, particularly preferred are openings with diamond-shaped cross section.

Preferentially the lancing depth reference element 8 consists of a plurality of components. The reference skin contact surface 11 is preferably formed on the plurality of components which are moveable relative to one another in order to provide a variation of the size of the element opening 9. The components of the lancing depth reference element are moved in such a manner that the movement comprises a movement component vertically to the lancing direction of the lancing movement. An example of such a lancing depth reference element 8 is for example diaphragm having a circular aperture with a modifiable cross section of the circular opening.

The two-piece shutter 44 in FIGS. 9*a* to 9*c* comprises two shutter elements 45 and 46. Shutter elements 45 and 46 can be moved relative to each other so that the shutter 44 can be completely closed (FIG. 9*a*). The completely closeable lancing depth reference element 8 can then close the entire lancing system 1, if the lancing depth reference element 8 is adapted to the housing opening 5 of the lancing device 2 in a closing and/or sealing manner.

FIG. 9*b* shows the shutter 44 of the lancing depth reference element 8 with a small element opening 9 from which the needle element 3 can emerge. FIG. 9*c* shows the completely opened shutter 44 wherein the two shutter elements 45 and 46 are separated from each other. An element opening 9 with a very large cross section is formed to allow collection of blood from the wound after lancing. In particular an analytical unit can be brought into the element opening 9 for taking up a drop of blood, the out-flowing blood being transported to a sample carrier.

FIG. 10 shows the shutter 44 in a lateral view. FIG. 10*a* shows the opened shutter wherein the two shutter elements 45, 46 are spaced from each other. On closing the shutter 44 the shutter elements 45, 46 are moved towards each other, while the shutter element 46 presses against the shutter element 45 and the latter against the housing 4 so that the housing opening 5 is closed.

FIGS. 11*a,b* and 12*a,b* show further embodiments of a lancing depth reference element 8 embodied as shutter 44. The multi-part shutter comprises an element opening 9. In the embodiment according to FIG. 11*b* the shutter parts 47 are radially moved outward by rotating the shutter 44 in order to enlarge the element opening 9.

In the embodiment according to FIGS. 12*a,b* the (for example) spring-loaded shutter parts 47 are held together by a clamp 48 which can be adjusted via a spindle 49. When the clamp 48 is widened, the shutter parts 47 are moved radially outward and the element opening 9 is enlarged, FIG. 12*b*.

FIGS. 13*a,b* show a lancing depth reference element 8 embodied in two parts whose two shutter elements 50, 51 can be pivoted relative to each other about a hinge 52. By this folding-open of the elements 50,51 the element opening 9 is enlarged so that after the lancing movement of the lancet or the needle element a large opening area is cleared into which an analytical unit can also be moved in order to take up the blood issuing from the wound following the lancing.

The lancing depth reference elements 8 with variable element openings 9 shown in FIGS. 9 to 13 are particularly suitable for blood extraction methods wherein the sample is not taken up by a needle element, but is collected on the skin surface in order to be directly taken up by an analytical element. Such blood extraction methods are carried out with a lancing system 1 which in addition to a lancing unit also comprises an analytical unit 54. The analytical unit 54 has at least one analytical element 55 to take up the fluid which preferably is the blood issuing from the finger 13. An analyte contained in the blood, in particular glucose, is determined in the analytical unit 54.

Such lancing devices with an integrated analytical unit are also known from WO 2005/006985 A2. Details of the preferentially cassette-like analytical unit with a band-shaped analytical element are described in detail in the mentioned publication and are therefore not explicitly explained at this point. The content of WO 2005/006985 A2 is embodied herein by reference.

For example FIG. 14 shows a lancing system 1 with an analytical unit 54 which is arranged in a lancing device 2. Behind the housing opening 5 of the lancing device 2 a multi-part lancing depth reference element 8 is arranged which is embodied in the form of the two-part shutter 44 known from FIG. 9.

The blood extraction sequence with the lancing device 2 differs significantly from the one described in FIGS. 2, 6 and 7. During its lancing movement in the forward phase, as well as during the return phase, the needle element 3 moves rapidly. In other words, it lances the finger 13 rapidly and likewise completely retreats from said finger just as rapidly. During the lancing process the lancing depth reference element 8 is substantially closed so that an element opening 9 is created whose cross section corresponds to a round cross section with a diameter of only approximately 2 mm.

Once the needle element 3 has been retracted from the skin 14 of the finger 13 the shutter elements 45 and 46 are each moved laterally in the direction of the arrow so that the element opening 9 is enlarged. Preferentially the size of the element opening 9 is then increased so far that it corresponds at least to the housing opening 5.

Due to the moving-apart of the shutter elements 45 and 46 of the lancing depth reference element 8, the finger 13 bulges further into the housing opening 5. At the same time, the counter pressure exerted by the lancing depth reference element 8 against the finger 13 is reduced or removed. Blood issuing from the wound is no longer prevented. The blood collected in the skin bulge of the finger can flow out of the lancing wound. An expression-promoting effect is thus achieved by the housing skin contact surface 7. The out flowing blood is ready to be taken up by the analytical element 55.

Once shutter elements 45 and 46 have been moved into their maximum opening position, analytical unit 54 is moved in the direction of the housing opening 5 in such a manner that blood flowing out from the lancing wound can be taken up by the analytical element 55.

Preferred is an embodiment of the lancing device 2 wherein the two shutter elements 45 and 46 are moved laterally relative to the lancing direction, wherein the lateral movement is defined in that it comprises a movement component perpendicular to the lancing direction. This includes a movement vertically to the lancing direction. The analytical unit 54 is preferably moved so that its movement comprises a movement component parallel to the lancing direction of the needle element 3. In addition, its movement can also have movement components oriented perpendicular to the lancing direction. In the simplest case the analytical unit 54 is moved parallel to the lancing direction of the needle element 3. On the movement path of the analytical unit it is moved from a starting position into a position behind the housing opening 5, while the analytical unit can then press against the finger 13 acting into the housing opening 5.

In an alternative embodiment the lancing depth reference element 8 may be embodied as one piece even in combination with a lancing device 2 with integrated analytical unit 54. In this case the lancing depth reference element 8 is preferably likewise moved laterally away from the housing opening 5, the movement comprising a movement component oriented vertically to the lancing direction. The movement can also take place diagonally towards the rear.

What is claimed is:

1. A lancing system for extracting a body fluid from the skin of a human or animal, comprising
a needle element for lancing the skin,
a lancing device, including a lancet drive by which a lancing movement of the needle element is driven in a lancing direction, the needle element being coupled with the lancet drive by means of a coupling mechanism,
wherein
the lancing device comprises a housing with a housing opening at a front end thereof and the housing opening is surrounded by a housing skin contact surface which is pressed against the skin during use of the lancing device,
the needle element is, during a forward phase of the lancing movement, moved on a predetermined lancing path in a lancing direction until a tip of the needle element enters the skin in order to create a wound and is again retracted in a return phase of the lancing movement after having reached a reversal point, the reversal point corresponding to the lancing depth in the skin,
a lancing depth reference element is provided for improving the reproducibility of the lancing depth the lancing depth reference element comprising a reference skin contact surface and being adapted and arranged in such a manner that the reference skin contact surface is, at the reversal point of the lancing movement, in contact with the skin and the predetermined value of the lancing depth is determined by the distance in lancing direction that exists at the reversal point of the lancing movement between the reference skin contact surface and the position of the tip of the needle element,
wherein
the lancing depth reference element is adapted and arranged in such a manner that during the lancing a skin-deformation-stabilizing compressive force acts between the reference skin contact surface and the skin, and
the skin-deformation-stabilizing compressive force is at most 7 N.

2. The lancing system according to claim 1, wherein the lancing system comprises a force sensor for measuring the compressive force which acts when the skin is pressed against the reference skin contact surface.

3. The lancing system according to claim 2, wherein the lancing device comprises a triggering lock such that the lancing process of the needle element can only be triggered when a predetermined minimum contact pressure is applied between the skin and the reference skin contact surface.

4. The lancing system according to claim 1, wherein the lancing depth reference element is mounted to be movable opposite to the lancing direction, wherein the force of a spring device acts in the lancing direction against a housing-fixed stop in such a manner that the lancing depth reference element is pressed against a housing-fixed stop and is displaced and lifted off the stop when the skin is pressed against the reference skin contact surface, the displacement being towards the rear against the force of the spring device and opposite to the lancing direction, wherein the compressive force acting on the skin corresponds to the spring force of the spring device.

5. The lancing system according to claim 1, wherein at least a part of the lancing depth reference element, on which the reference skin contact surface is formed, is a disposable element intended for once only use.

6. The lancing system according to claim 1 wherein the return phase of the lancing movement includes two part sections wherein the movement of the needle element is faster in the first part section than in the second part section and wherein during the rapid movement of the first part section of the return phase the reference skin contact surface remains in a stationary position.

7. The lancing system according to claim 1 wherein during a part of the return phase the lancing depth reference element is moved simultaneously with the needle element away from the skin.

8. The lancing system according to claim 7 wherein the lancing depth reference element and the needle element are moved in synchronization during a part of the return phase in such a manner that the relative distance between the tip of the needle element and the reference skin contact surface of the lancing depth reference element remains unchanged.

9. The lancing system according to claim 1 wherein before the tip of the needle element is completely extracted from the skin, the lancing depth reference element is moved from a stationary position relative to the housing and opposite to the lancing direction only so far that the reference skin contact surface remains in contact with the skin.

10. The lancing system according to claim 1 wherein the lancing depth reference element is adapted and arranged in such a manner that the lancing depth reference element is located in a defined stationary position relative to the housing before the skin is pressed against the housing skin contact surface.

11. The lancing system according to claim 1, wherein the lancet drive comprises a drive rotor, the needle element being driven by the rotary movement of the drive rotor.

12. The lancing system according to claim 11, wherein the lancet drive comprises a two-part drive rotor, one part being axially displaceable relative to the other part for adjusting the lancing depth of the needle element.

13. The lancing system according to claim 11, wherein the lancet drive comprises a tensioning rotor which is coupled with the drive rotor in such a manner that the drive rotor on a part of its movement is moved in synchronization with the tensioning rotor.

14. The lancing system according to claim 13, wherein the tensioning rotor comprises a control curve by means of which a traveler is guided the traveler being coupled with the lancing depth reference element via a coupling mechanism.

15. The lancing system according to claim 1, wherein the needle element comprises a capillary channel through which a body fluid can be transported out of the skin.

16. The lancing system according to claim 1, wherein the lancing device is adapted for multiple use and includes a holder by means of which a lancing unit can be interchangeably coupled with the lancet drive, wherein the reference skin contact surface of the lancing depth reference element is embodied on a disposable single-use element.

17. The lancing system according to claim 1, wherein the lancing depth reference element comprises an element opening through which the tip of the needle element extends in the forward phase of the lancing movement and the element opening being arranged such that the smallest distance between the needle element and the reference skin contact surface of the lancing depth reference element measured vertically to the lancing direction, is at most 2 mm.

18. The lancing system according to claim 17, wherein the element opening of the lancing depth reference element is variable in its size.

19. The lancing system of claim 17, wherein the smallest distance between the needle element and the reference skin contact surface of the lancing depth reference element measured vertically to the lancing direction is at most 1 mm.

20. The lancing system of claim 19, wherein the smallest distance between the needle element and the reference skin contact surface of the lancing depth reference element measured vertically to the lancing direction is at most 0.5 mm.

21. The lancing system according to claim 1, wherein the reference skin contact surface is embodied on a plurality of components.

22. The lancing system according to claim 21, wherein:
the lancing depth reference element comprises an element opening through which the tip of the needle element extends in the forward phase of the lancing movement and the element opening being arranged such that the smallest distance between the needle element and the reference skin contact surface of the lancing depth reference element measured vertically to the lancing direction, is at most 2 mm; and
the plurality of components is moveable relative to one another for varying the size of the element opening of the lancing depth reference element.

23. The lancing system of claim 22, wherein the smallest distance between the needle element and the reference skin contact surface of the lancing depth reference element measured vertically to the lancing direction is at most 1 mm.

24. The lancing system of claim 23, wherein the smallest distance between the needle element and the reference skin contact surface of the lancing depth reference element measured vertically to the lancing direction is at most 0.5 mm.

25. The lancing system according to claim 1, wherein the lancing system comprises an analysis unit which comprises at least one analysis element for taking up a fluid and for determining an analyte contained in the fluid.

26. The lancing system according to claim 1, wherein the skin-deformation-stabilizing compressive force is at most 5 N.

27. The lancing system according to claim 1, wherein the skin-deformation-stabilizing compressive force is at least 2 N.

28. The lancing system according to claim 1, wherein the skin-deformation-stabilizing compressive force is at least 3 N.

29. Lancing system for extracting a body fluid from the skin of a human or animal, comprising:
a needle element for lancing the skin;
a lancing device, including a lancet drive by which a lancing movement of the needle element is driven in a lancing direction, the needle element being coupled with the lancet drive by means of a coupling mechanism;
wherein
the lancing device comprises a housing with a housing opening at a front end thereof and the housing opening is surrounded by a housing skin contact surface which is pressed against the skin during use of the lancing device;
the needle element is, during a forward phase of the lancing movement, moved on a predetermined lancing path in the lancing direction until a tip of the needle element enters the skin in order to create a wound and is again retracted in a return phase of the lancing movement after having reached a reversal point, the reversal point corresponding to the lancing depth in the skin; and
a lancing depth reference element is provided for improving the reproducibility of the lancing depth, the lancing depth reference element comprising a reference skin contact surface and being adapted and arranged in such a manner that the reference skin contact surface is, at the reversal point of the lancing movement, in contact with the skin and the predetermined value of the lancing depth is determined by the distance in the lancing direction that exists at the reversal point of the lancing movement between the reference skin contact surface and the position of the tip of the needle element;
wherein the needle element comprises a capillary channel through which a body fluid can be transported out of the skin;

during a part of the return phase the lancing depth reference element is moved simultaneously with the needle element away from the skin; and after the reversal point of the lancing movement the needle element is moved opposite to the lancing direction to a defined residual lancing depth and thereafter the simultaneous movement of the lancing depth reference element and the needle element takes place with the needle element projecting from reference skin contact surface of the lancing depth reference element.

30. The lancing system according to claim 29, wherein the simultaneous movement of the lancing depth reference element and the needle element takes place before the tip of the needle element is completely pulled out of the skin.

31. The lancing system according to claim 29, wherein the lancing depth reference element with the reference skin contact surface is in a defined start position with respect to the housing skin contact surface before the lancing system contacts the skin.

32. The lancing system according to claim 31, wherein the start position of the lancing depth reference element with the reference skin contact surface, relative to the housing skin contact surface, is defined by the contact of a stop of the lancing depth reference element with a corresponding housing stop.

33. The lancing system according to claim 29, wherein the lancing depth reference element and the needle element are moved in synchronization during a part of the return phase in such a manner that the relative distance between the tip of the needle element and the reference skin contact surface of the lancing depth reference element remains unchanged.

34. The lancing system according to claim 29, wherein the return phase of the lancing movement includes two part sections wherein the movement of the needle element is faster in the first part section than in the second part section and wherein during the faster movement of the first part section of the return phase the reference skin contact surface remains in a stationary position.

35. The lancing system according to claim 29, wherein before the tip of the needle element is completely extracted from the skin, the lancing depth reference element is moved from a stationary position relative to the housing and opposite to the lancing direction only so far that the reference skin contact surface remains in contact with the skin.

36. The lancing system according to claim 29, wherein the lancing depth reference element comprises an element opening through which the tip of the needle element extends in the forward phase of the lancing movement and the element opening is arranged such that the smallest distance between the needle element and the reference skin contact surface of the lancing depth reference element measured vertically to the lancing direction, is at most 2 mm.

37. The lancing system according to claim 36, wherein the smallest distance between the needle element and the reference skin contact surface of the lancing depth reference element measured vertically to the lancing direction, is at most 1 mm.

38. The lancing system according to claim 37, wherein the smallest distance between the needle element and the reference skin contact surface of the lancing depth reference element measured vertically to the lancing direction, is at most 0.5 mm.

39. The lancing system according to claim 29, comprising an analysis unit which comprises at least one analysis element for taking up a fluid and for determining an analyte contained in the fluid.

\* \* \* \* \*

UNITED STATES PATENT AND TRADEMARK OFFICE
CERTIFICATE OF CORRECTION

| | |
|---|---|
| PATENT NO. | : 8,444,574 B2 |
| APPLICATION NO. | : 12/396838 |
| DATED | : May 21, 2013 |
| INVENTOR(S) | : Hans List |

It is certified that error appears in the above-identified patent and that said Letters Patent is hereby corrected as shown below:

In the Specification

Col. 6, line 32, replace "one-step-andling" with --one-step-handling--

Signed and Sealed this
Twenty-fifth Day of June, 2013

Teresa Stanek Rea
*Acting Director of the United States Patent and Trademark Office*